United States Patent [19]

Costerousse et al.

[11] Patent Number: 4,908,359
[45] Date of Patent: Mar. 13, 1990

[54] 1-DETHIA-2-THIA-CEPHALOSPORANIC ACIDS

[75] Inventors: Germain Costerousse, Saint-Maurice; Solange Gouin d'Ambrieres, Paris; Jean-Georges Teutsch, Pantin, all of France

[73] Assignee: Roussel Uclaf, Paris, France

[21] Appl. No.: 153,148

[22] Filed: Feb. 8, 1988

[30] Foreign Application Priority Data

Feb. 6, 1987 [FR] France ............................ 87 01457

[51] Int. Cl.$^4$ .................... C07D 417/12; A61K 31/54
[52] U.S. Cl. ..................................... 514/210; 540/214
[58] Field of Search ................ 540/214, 215; 514/210

[56] References Cited

U.S. PATENT DOCUMENTS 4,476,124 10/1984 Heymes et al. ...................... 540/214

Primary Examiner—Nicholas S. Rizzo
Attorney, Agent, or Firm—Bierman and Muserlian

[57] ABSTRACT 1-dethia-2-thia-cephalosporanic acids of the formula

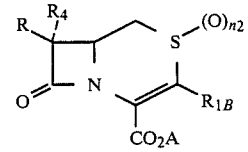

wherein R is selected from the group consisting of

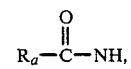

$R_b$—NH—and

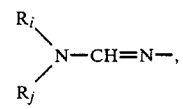

$R_a$ is an organic radical $R_i$ and $R_j$ are individually selected from the group consisting of hydrogen, aliphatic, aromatic and heterocycle or taken together with the nitrogen atom form an optionally substituted heterocycle, $R_b$ is optionally substituted carbocyclic or heterocyclic aryl, $R_{1B}$ is —[CH=CH]$_{n1}$—CH$_2$—S—R$_m$, $n_1$ is 0, 1 or 2, Rm is an unsaturated radical including a positively charged and doubly bonded nitrogen atom and bonded to the sulfur atom through a carbon atom, $R_4$ is hydrogen or methoxy, $n_2$ is 0, 1 or 2 and A is selected from the group consisting of hydrogen, alkali metal ion, or alkaline earth metal ion, magnesium ion, ammonium ion, an organic amine base and an ester group or —COOA is —COO$^-$ and their non-toxic, pharmaceutically acceptable acid addition salts, having antibiotic activity.

15 Claims, No Drawings

1-DETHIA-2-THIA-CEPHALOSPORANIC ACIDS

STATE OF THE ART

Related references are U.S. patent application Ser. No. 700,690 filed Feb. 12, 1985 and U.S. patent application Ser. No. 895,175 filed Aug. 11, 1986.

OBJECTS OF THE DISCLOSURE

It is an object of the invention to provide the novel compounds of formula I and their salts and a method for their preparation.

It is another object of the invention to provide novel antibiotic compositions and a novel method of combatting bacterial infections in warm-blooded animals.

These and other objects and advantages of the invention will become obvious from the following detailed description.

THE INVENTION

The novel compounds of the invention are 1-dethia-2-thia-cephalosporanic acids of the formula

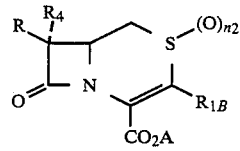

wherein R is selected from the group consisting of

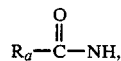

$R_b$—NH— and

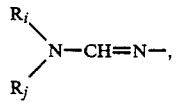

$R_a$ is an organic radical $R_i$ and $R_j$ are individually selected from the group consisting of hydrogen, aliphatic, aromatic and heterocycle or taken together with the nitrogen atom form an optionally substituted heterocycle, $R_b$ is optionally substituted carbocyclic or heterocyclic aryl, $R_{1B}$ is —[CH═CH]$_{n1}$—CH$_2$—S—R$_m$, $n_1$ is 0, 1 or 2, Rm is an unsaturated radical including a positively charged and doubly bonded nitrogen atom and bonded to the sulfur atom through a carbon atom, $R_4$ is hydrogen or methoxy, $n_2$ is 0, 1 or 2 and A is selected from the group consisting of hydrogen, alkali metal ion, or alkaline earth metal ion, magnesium ion, ammonium ion, an organic amine base and an ester group or —COOA is —COO$^-$ and their non-toxic, pharmaceutically acceptable acid addition salts.

Among the preferred compounds of formula I are those wherein R is anacylamino of the formula

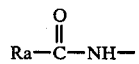

wherein Ra is an organic radical. Examples of Ra are:

(1) Ar—(CH$_2$)$_n$—,

Ar—CH$_2$O—, Ar—OCH$_2$, Ar—S—CH$_2$—Ar—CH$_2$—S— and

wherein Ar is an optionally mono- or poly-substituted phenyl or an aromatic heterocyclic of 5,6 or 7 links having 1 to 4 heteroatoms chosen from sulfur, oxygen and nitrogen, n is an integer from 0 to 4, $R_5$ is amino, hydroxyl, azido, hydrazino, free, esterified or salified carboxyl, sulfo, free or salified, sulfoamino, halogen, alkyl hydrazino, phenyl hydrazino, or formyloxy.

Among the substituents of the phenyl or heterocyclic are halogens and alkyl and alkoxy of 1 to 4 carbon atoms aminoalkyl of 1 to 4 carbon atoms, preferably aminomethyl, hydroxyl, nitro, amino, trifluoromethyl or cyano. Among the heterocyclic aromatics are: thiazolyl, furyl, thienyl, pyrrolyl, pyridinyl, pyrazinyl, morphonyl and tetrazolyl. Furyl, aminothiazolyl, aminohalothiazolyl, aminothiadiazolyl and aminopyramidinyl are preferred.

(2) Ra can also be alkyl, cycloalkyl, alkoxy, alkenyl, or cycloalkenyl, each of which can also be optionally mono- or poly-substituted by at least one substituent such as alkylthio or cyanoalkylthio, mercapto, nitro, cyano or amino.

(3) Ra can also be:

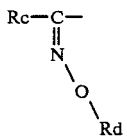

Rc can have the same definition as Ar and among the preferred values for Rc are 2-amino-4-thiazolyl; 2-amino-5-nitro, -5-chloro, -5-fluoro or -5-bromothiazolyl; 5-amino-1,2,4-thiadiazolyl, -4-thiazolyl, -2-thienyl or -2-furyl; Rd is hydrogen, acyl, aryl, heteroaryl, arylalkyl, heteroarylalkyl, alkyl, cycloalkyl, alkenyl, cycloalkenyl or alkynyl optionally substituted and optionally interrupted by oxygen or an optionally oxidized sulfur, or Rd can be optionally substituted carbamoyl.

Among the substituents of Rd are alkyl, halogen, acyl, cyano, carbamoyl, nitro, amino, hydroxy, mercapto, alkylthio, oxo, and alkoxy radicals, and a free, esterified or salified carboxy. Among the values of Rd are hydrogen, alkyl, alkenyl, possibly cyclic, alkynyl, aryl, mono- or polycyclic heteroaryl and particularly

—CH$_3$, —CH$_2$—CH$_3$, —CHF$_2$, —CH$_2$—CF$_3$,

—CH$_2$—O—CH$_3$, —CH$_2$—S—CH$_3$, —CH$_2$—S—CH$_3$,
$$\downarrow$$
$$O$$

—CH$_2$—SO$_2$—CH$_3$, —CH$_2$CN, —CH$_2$—CONH$_2$, —CH$_2$—,

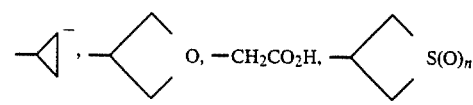

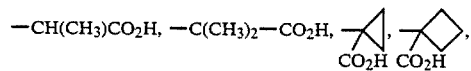

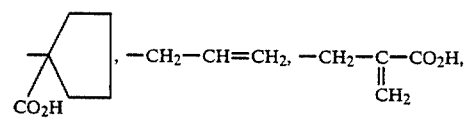

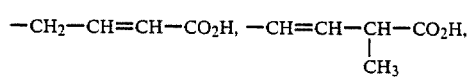

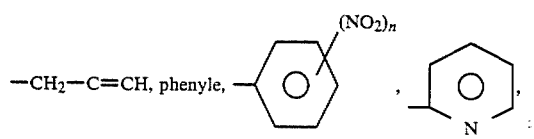

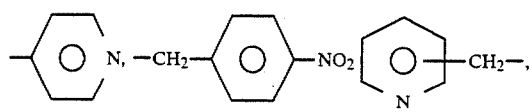

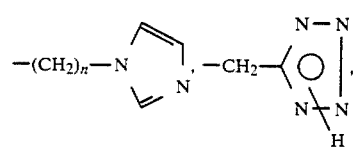

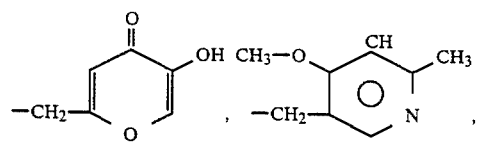

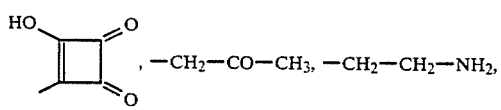

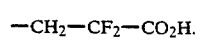

Among the values for Rd, methyl, hydrogen, ethyl, allyl, 1-methyl-1-carboxyethyl, carboxymethyl or difluoromethyl are preferred.

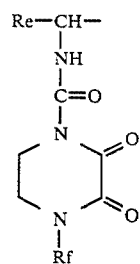

(4) Ra may also be

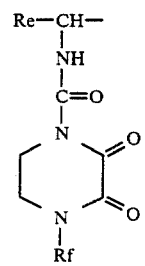

wherein Re has the same values as Ar, but unsubstituted phenyl is preferred. Rf may be an optionally substituted alkyl or —N═CH—Rg in which Rg is aryl as defined above for Ra. Rf is preferred to be ethyl, phenyl or furyl.

(5) Ra may also be

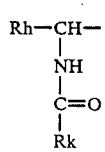

wherein Rh has the values indicated for Ar and Rk may be

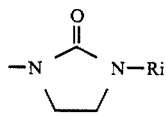

in which Ri is hydrogen, alkylsulfonyl or —N═CH—Rm where Rm has the same value as Ar, particularly furyl: Rk can be an optionally substituted aryl, for example, an imidazolyl substituted by a carboxyl: Rk may also be substituted amino, for example, an acylamido such as N-methylbenzoylamido or furylcarbonyl or an amino substituted by an optionally substituted heterocycle; Rk may also be an optionally substituted and condensed aryl and an optionally substituted aralkyl.

In this first class of products, those are preferred wherein Ra has the following values.

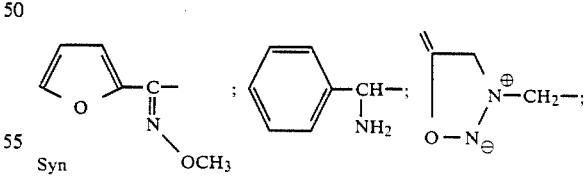

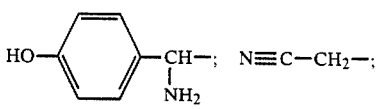

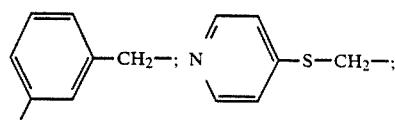

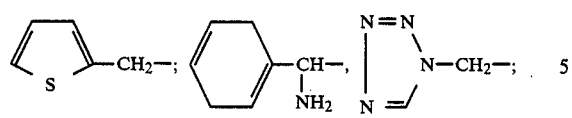
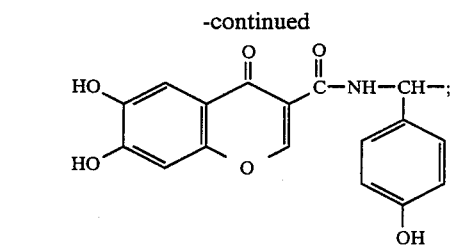
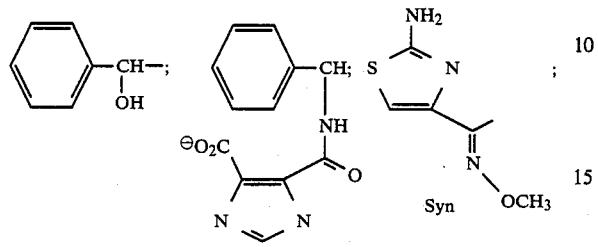
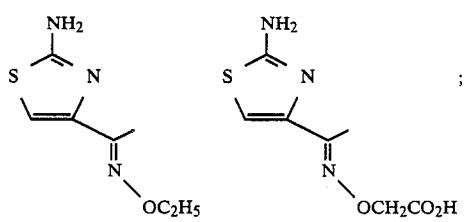
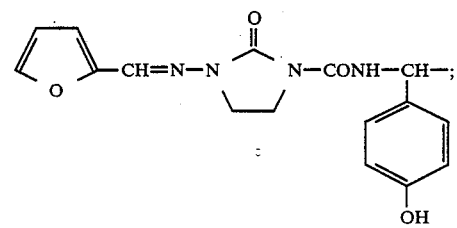
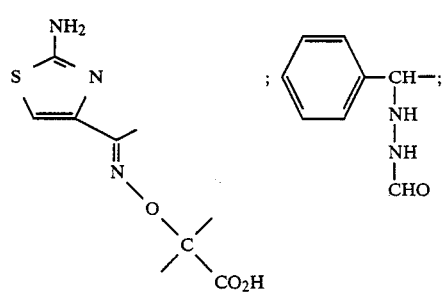
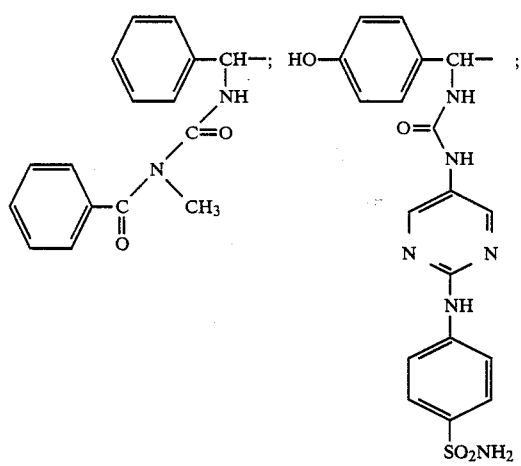
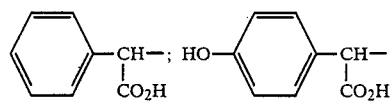
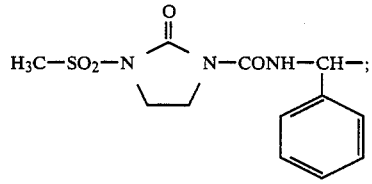
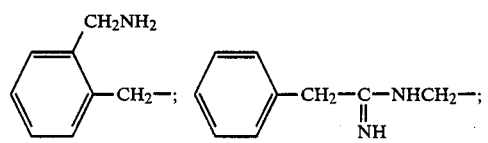
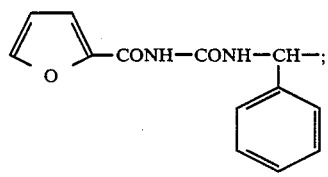
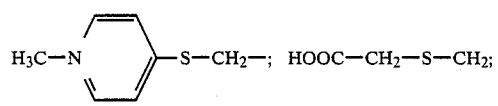
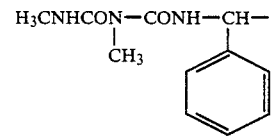
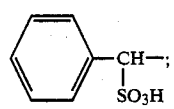
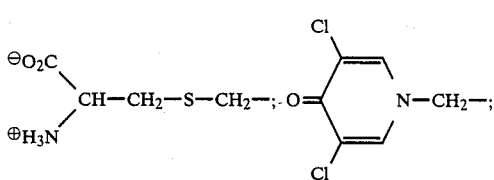

-continued
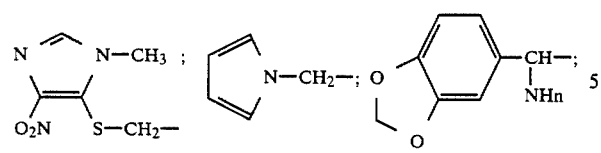
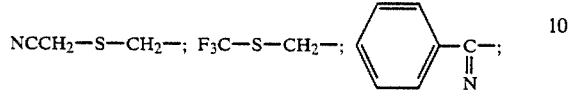
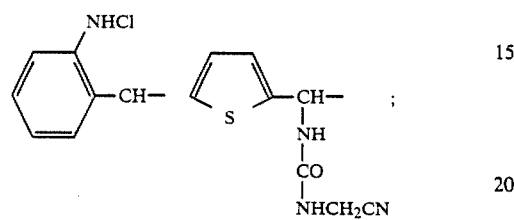
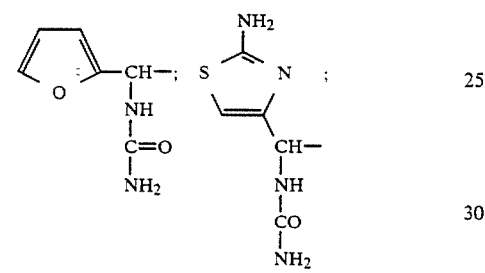
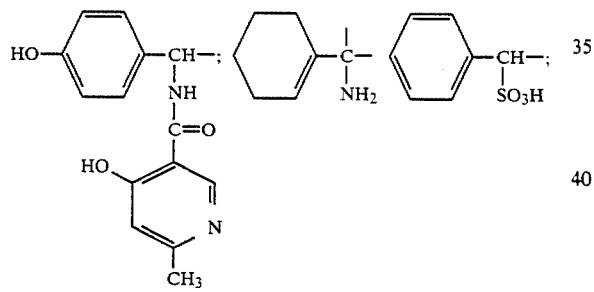
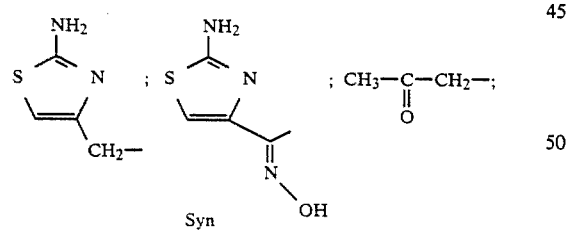
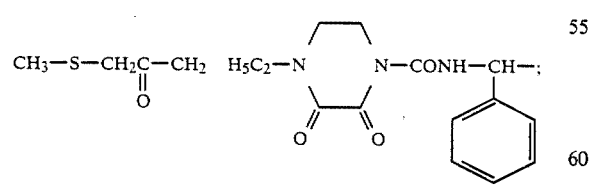
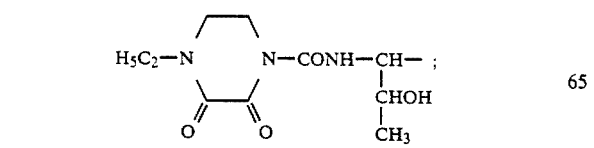
-continued
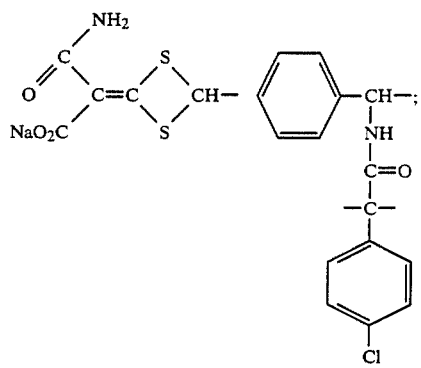
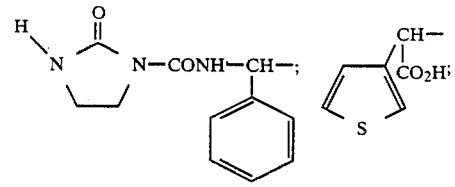
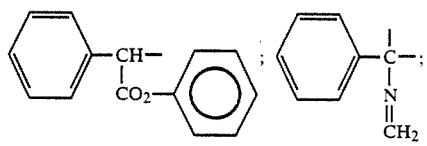
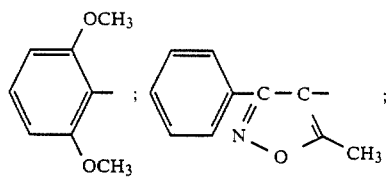
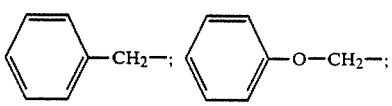
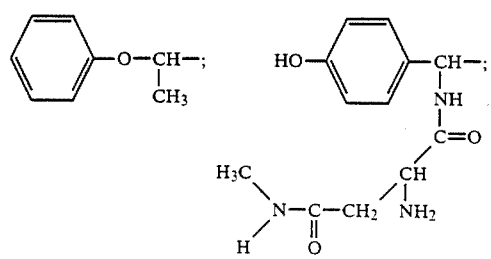
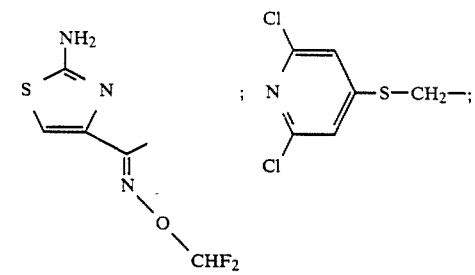

-continued

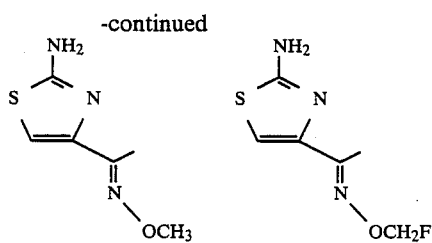

In this first class of products, those are preferred wherein Ra has the following values.

Among other preferred values for R is

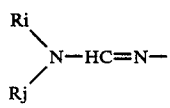

wherein Ri and Rj are individually selected from the group consisting of hydrogen and alkyl of 1 to 8 carbon atoms, or Ri and Rj may form with the nitrogen atom to which they are attached an optionally substituted cyclic amine. Preferably,

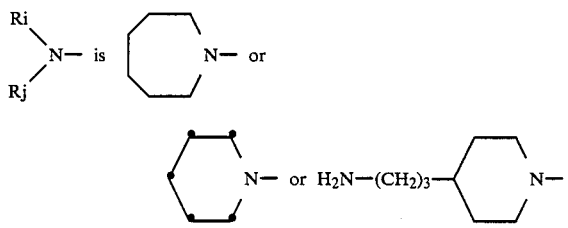

Another preferred value A is Rb—NH— in which Rb is optionally substituted carbocyclic or heterocyclic aryl. Among these preferred values for R are

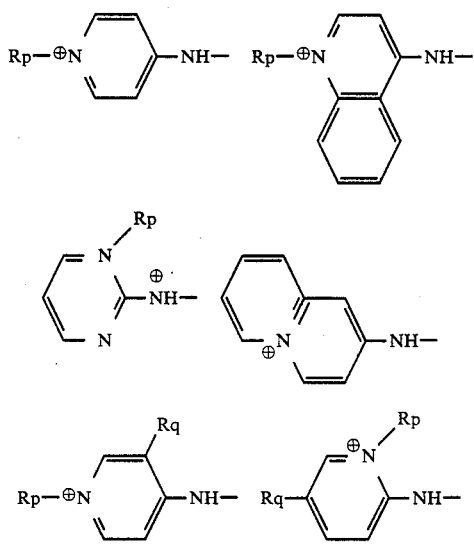

in which Rp is alkyl of 1 to 4 carbon atoms, preferably methyl, ethyl, isopropyl possibly interrupted by a heteroatom such as methoxymethyl, optionally substituted by at least one halogen such as trichloroethoxy methyl or trifluoroethoxy methyl and alkoxy such as ethoxy. Rp may also be arylalkyl such as benzyl or phenethyl, optionally substituted by alkyl such as methyl, alkoxy such as methoxy, cyano and halogen such as fluoro. Rp may also be furfuryl or an optionally substituted phenylmethoxymethyl. Rq may be hydrogen or alkyl of 1 to 4 carbon atoms such as methyl, an alkoxycarbonyl such as methoxy carbonyl or tert-butoxy carbonyl.

Among the preferred values for R is

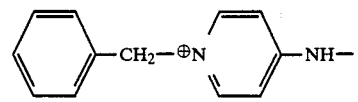

Rm is an unsaturated radical including a positively charged and doubly bonded nitrogen, the said radical being attached to the sulfur atom through one of the carbon atoms.

Among the values for Rm are heterocyclic groups containing a positively charged nitrogen atom which can be a simple or condensed ring. Preferably, it is an aromatic group. Rm may also be linear groups such as

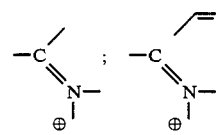

Among the heterocyclic groups are pyridyl optionally substituted by one or more members chosen from alkyl of 1 to 4 carbon atoms such as methyl, ethyl, propyl, isopropyl, butyl, sec-butyl, tert-butyl, alkoxy such as methoxy, ethoxy, halogen such as bromine, chlorine, iodine or fluorine, carboxyalkyl optionally esterified, or carbamoyl, and thioacetylalkyl, thiocarbamoylalkyl, haloalkyl, cyanoalkyl, alkenyl of 2 to 4 carbon atoms such as allyl, alkylthioalkyl and thioalkyl.

Examples of heterocyclic are pyrrolyl, oxazolyl, thiazolyl, imidazolyl, pyrazolyl, triazolyl, tetrazolyl, pyridazinyl, pyrimidinyl, pyrazinyl, quinoleinyl, isoquinoleinyl, cinnolinyl, quinazolinyl, pyridino [1,2-a] pyrimidinyl, as well as partially hydrogenated derivatives such as dihydro- or tetrahydro-pyridyl. The heterocycles may also be substituted by one or more of the members indicated for pyridyl.

The preferred values for Rm are:

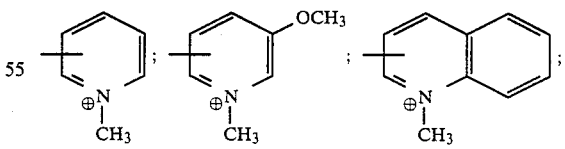

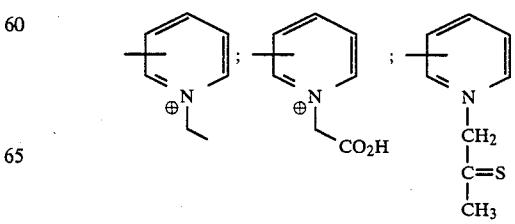

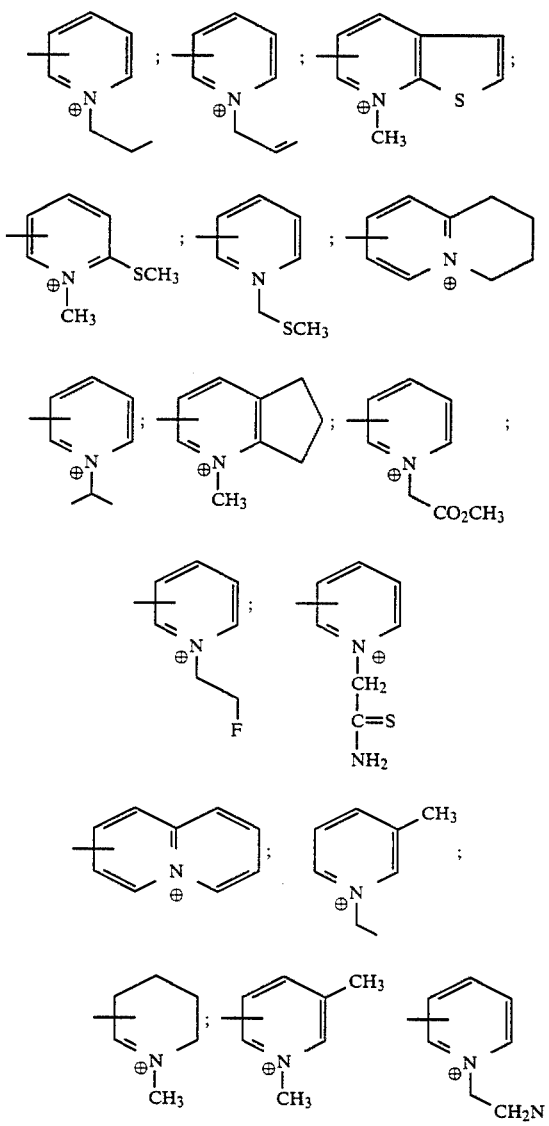

Examples of A are sodium, potassium, lithium, calcium, magnesium, ammonium, or of an organic base such as methylamine, propylamine, trimethylamine, diethylamine, triethylamine, N,N-dimethylethanolamine, tris(hydroxymethylamino-methane), ethanolamine, pyridine, picoline, dicyclohexylamine, morpholine, benzylamine, procaine, lysine, arginine, histidine and N-methylglucamine.

Among other residues of easily cleavable ester groups which A may be are: methoxymethyl, ethoxymethyl, isopropyloxymethyl, α-methoxyethyl, α-ethoxyethyl, methylthiomethyl, ethylthiomethyl, isopropylthiomethyl, pivaloyloxymethyl, acetoxymethyl, propionyloxymethyl, butyryloxymethyl, isobutyryloxymethyl, valeryloxymethyl, isovaleryloxymethyl, tert-butyl-carbonyloxymethyl, hexadecanoyloxymethyl, propionyloxyethyl, isovaleryloxyethyl, 1-acetyloxyethyl, 1-propionyloxyethyl, 1-butyryloxyethyl, 1-tert-butylcarbonyloxyethyl, 1-acetyloxypropyl, 1-hexadecanoyloxyethyl, 1-propionyloxypropyl, 1-methoxycarbonyloxyethyl, methoxycarbonyloxymethyl, 1-acetyloxybutyl, 1-acetyloxyhexyl, 1-acetyloxyheptyl, phthalidyl, 5,6-dimethoxyphthalidyl, tert-butyl-carbonylmethyl, allyl, 2-chloroallyl, methoxycarbonylmethyl, benzyl or tert-butyl.

Among other residues of ester groups which A may be are: methoxyethoxymethyl, dimethylaminoethyl, cyanomethyl, tert-butyloxycarbonylmethyl, 2,2-ethylenedioxyethyl, cyanoethyl, 2,2-dimethoxyethyl, 2-chloroethoxymethyl, 2-hydroethoxyethyl, 2,3-epoxypropyl, 3-dimethylamino, 2-hydroxypropyl, 2-hydroxyethyl, 2-methylaminoethoxymethyl, 2-aminoethoxymethyl, 3-methoxy-2,4-thiadiazol-5-yl, 2-tetrahydropyranyl, 2-methoxyprop-2-yl, 1-hydroxyprop-2-yl, isopropyl, carbamoylmethyl, chloromethyl, 2-chloroethyl, acetylmethyl, 2-methylthioethyl or thiocyanatomethyl.

Among other residues of ester groups which A may be are: 2-chloro-1-acetyloxyethyl, 2-bromo-1-acetyloxyethyl, 2-fluoro-1-acetyloxyethyl, 2-methoxy-1-acetyloxyethyl, 2-methyl-1-acetyloxypropyl, 2-acetyloxypropy-2-yl, 1-methoxyacetyloxyethyl, 1-acetylcarbonyloxyethyl, 1-hydroxyacetyloxyethyl, 1-formylcarbonyloxyethyl, 1-(2-thienyl)-carbonyloxyethyl, 1-(2-furyl)-carbonyloxyethyl, 1-(5-nitro-2-furyl)-carbonyloxyethyl, 1-(2-pyrrolyl)-carbonyloxyethyl, 1-(propionyloxycarbonyloxy)-ethyl, 1-(propyloxycarbonyloxy)-ethyl, 11-(isopropyloxycarbonyloxy)-ethyl, 1-(methoxyethoxycarbonyloxy)-ethyl, 1-(allyloxycarbonyloxy)-ethyl, 1-(2,3-epoxy)-propyloxycarbonyloxyethyl, 1 -(2-furyl)-methoxycarbonyloxyethyl, 1(2-fluoro)-ethyloxycarbonyloxyethyl, 1-(methoxycarbonyloxy)-propyl, (2-methoxycarbonyloxy-prop-2-yl), (methoxycarbonyloxy)-chloromethyl, 1-(methoxycarbonyloxy)-2-chloroethyl and 1-(methoxycarbonyloxy)-2-methoxycarbonyloxy)-1-allyl. A may also be

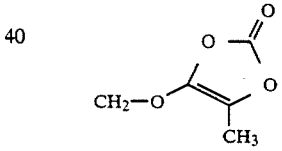

The products of formula I can also be in the form of salts of non-toxic, pharmaceutically acceptable organic or mineral acids. Among the acids are: trifluoroacetic acid, maleic acid, tartaric acid, methanesulfonic acid, benzene sulfonic acid, p-toluene sulfonic acid, trilfluoromethanesulfonic acid, formic acid, phosphoric acid, sulfuric acid, hydrochloric acid, hydrobromic acid, hydriodic acid.

Among the values for A are the ester of the formula:

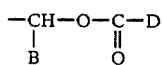

in which B is hydrogen or optionally substituted alkyl of 1 to 5 carbon atoms, and D is optionally substituted alkyl or alkoxy of 1 to 15 carbon atoms, and particularly from 1 to 5 carbon atoms, and more particularly, the ester groups in which B is hydrogen or methyl or ethyl and D is methyl, ethyl, methoxy or ethoxy.

Among other values for A are

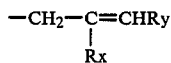

in which Rx is hydrogen, alkyl, particularly methyl and ethyl, halogen, particularly chlorine, and Ry is hydrogen, halogen, aryl, particularly phenyl, optionally substituted by methyl, methoxy or halogen, or Ry is alkyl optionally substituted by acyloxy, alkoxycarbonyl or halogen.

Among other values for A are:

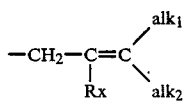

in which Rx is defined as above and alk$_1$ and alk$_2$ are individually alkyl of 1 to 4 carbon atoms.

Among the preferred products of formula I are compounds of the formula in the syn isomer form.

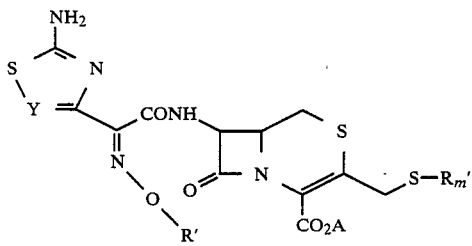

I' wherein R' is hydrogen or alkyl, alkenyl, alkynyl or cycloalkyl of up to 6 carbon atoms optionally substituted or aryl, R$_m$' is pyridinium optionally substituted, partially hydrogenated or forming part of a condensed ring bonded to the sulfur atom through a carbon atom, Y is methine or nitrogen and A has the significance indicated above.

Among the preferred compounds of formula I' are those in which R' is hydrogen, or methyl or isopropyl optionally substituted by a carboxy, carbamoyl, nitrile, methylthio or methoxy, fluoromethyl, difluoromethyl or trifluoromethyl, phenyl, cyclobutyl or cyclopropyl optionally substituted by carboxy, alkyl optionally substituted by chlorine or bromine, propenyl optionally substituted by halogen such as bromine, or cyclopropylmethyl.

More preferred compounds of the invention are those of the formula

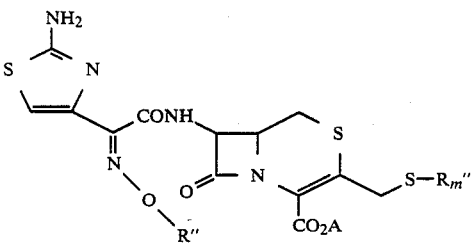

I'' in which R'' is methyl, fluoromethyl or difluoromethyl, R$_m$'' is

in which Alk is alkyl of 1 to 4 carbon atoms, R$_5$ is hydrogen, alkyl or alkylthio of 1 to 4 carbon atoms, R$_m$'' is bonded to the sulfur atom by the positions 2 or 4 and A has the significance indicated above.

Among specific preferred compounds are (6S)(7S)(Z) 4-[[[7-[[(2-amino-4-thiazolyl)-[(difluoromethoxy) -imino]-acetamido]-2-carboxy-8-oxo-4-thia-1-azabicyclo[4,2,0]oct-2-en-3-yl]-methyl]-thio]-1-methyl pyridinium, (6S)(7S)(Z) 4-[[[7-[[(2-amino-4-thiazolyl)-[(fluoromethoxy]-acetamido]-2-carboxy-8-oxo-4-thia-1-azabicyclo[4,2,0]oct-2-en-3-yl]-methyl]-thio]-1-methyl pyridinium, (6S)(7S)(Z) 2-[[[7-[[(2-amino-4-thiazolyl)-[(fluoromethoxy) -imino]-acetamido]-2-carboxy-8-oxo-4-thia-1-azabicyclo[4,2,0]oct-2-en-3-yl]-methyl]-thio]-1-methyl pyridinium, (6S)(7S)(Z) 4-[[[7-[[2-(2-amino-4-thiazolyl)-2-(methoxy) -imino]-acetamido]-2-carboxy-8-oxo-4-thia-1-azabicyclo[4,2,0]oct-2-en-3-yl]-methyl]-thio]-1-ethyl-3-methyl pyridinium (6S)(7S)(Z) 4-[[[7-[[2-(2-amino-4-thiazolyl)-2-(methoxy)-imino]-acetamido]-2-carboxy-8-oxo-4-thia-1-azabicyclo[4,2,0]oct-2-en-3-yl]-methyl]-thio]-1,3-dimethyl pyridinium, (6S)(7S)(Z) 4-[[[7-[[(2-amino-4-thiazolyl) (methoxy)-imino]-acetamido]-2-carboxy-8-oxo-4-thia-1-azabicyclo[4,2,-0]oct-2-en-3-yl]-methyl]-thio]-1-methyl pyridinium, (6S)(7S)(Z) 4-[[[7-[[2(2-amino-4-thiazolyl) (methoxy)-imino]-acetamido]-2-carboxy-8-oxo-4-thia-1-azabicyclo[4,2,0]oct-2-en-3-yl]-methyl]-thio]-1-methyl-5,6-dihydro pyridinium in the form of an internal salt or of acid addition salts which mineral or organic acids Most preferred is (6S)(7S)(Z) 4-[[[7-[[(2-amino-4-thiazolyl]-[(difluoromethoxy) -imino-acetamido]-2-carboxy-8-oxo-4-thia]-1-azabicyclo[4,2,0]-oct-2-en-3-yl]methyl]-thio]-1-methyl pyridinium, in the form of an internal salt or of acid addition salts with mineral or organic acids.

The process of the invention for the preparation of the products of formula I comprises reacting a product of the formula

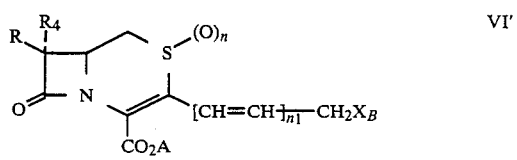

VI' in which R, R$_4$, A, n$_1$ and n$_2$ have the significance indicated above and X is halogen or a pseudo halogen with a product of the formula

R$_{AM}$CS          VIII in which R$_{AM}$ is the residue of the radical R$_m$ in which the nitrogen atom is bonded by simple, non-polar bonds and if necessary or if desired, the product obtained is submitted to any one or more of the following reactions in any order:

(a) cutting-off by hydrolysis, hydrogenolysis or by the action of thiourea of all or part of the protector group or groups;

(b) esterification or salification by a base of the carboxy or sulfo group or groups;

(c) salification by an acid of the amino group or groups;

(d) resolution of the molecule to obtain an optically active product;

(e) oxidation of the sulfur in position 2 of the isocephem ring.

X may be halogen such as chlorine or iodine or a pseudo halogen such as tosyloxy. In the product of formula VIII, $R_{AM}$ is the residue of $R_m$ in which the carbon atom by which the said radical $R_m$ is bonded to the sulfur atom is extracted for convenience of writing. $R_{AM}$, the nitrogen atom is bonded by simple bonds and is non-polar. For example, if $R_m$ is 2- or 4-methyl pyridinium of the formula

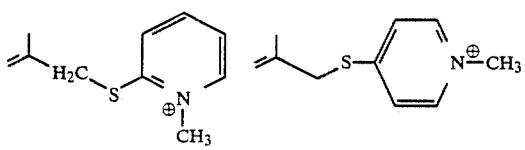

$R_{AM}$ is

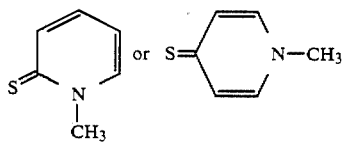

The reaction of the products of formula VIII with the products of formula VI' is preferably carried out at ambient temperature in a solvent such as acetonitrile or methylene chloride. When the products obtained include protector groups which it is desired to eliminate, the said products are treated with one or more hydrolysis or hydrogenolysis agents or with thiourea. The nature of the reagents used in all of these cases is well known to any expert and examples of such reactions are given further on.

A non-exhaustive list is now given of the means which can be put to work to eliminate the different groups. Acid hydrolysis is used preferably to eliminate the optionally substituted alkoxy and cycloalkoxycarbonyl such as tert-pentyloxycarbonyl or tert-butyloxycarbonyl, the optionally substituted aralkoxycarbonyl such as benzyloxycarbonyl, trityl, benzhydryl, tert-butyl or 4-methoxybenzyl. The acid preferably used can be chosen from the group consisting of hydrochloric acid, benzene sulfonic acid or p-toluene sulfonic acid, formic acid or trifluoroacetic acid but other mineral or organic acids can be used.

Basic hydrolysis is preferably used to eliminate the acyl groups such as trifluoroacetyl. The base preferably used is a mineral base such as sodium or potassium hydroxide but also may be used magnesia, baryta or a carbonate or bicarbonate of an alkali metal such as the carbonate or bicarbonate of sodium or potassium or other bases. Sodium or potassium acetate can also be used. Hydrolysis using hydrazine is preferably used to eliminate groups such as phthaloyl.

Certain groups can also be eliminated by the zinc-acetic acid system for trichloroethyl and benzhydryl, and benzyloxycarbonyl are preferably eliminated by hydrogen in the presence of a catalyst. The chloroacetyl group is eliminated by the action of thiourea in a neutral or acid medium by the reaction described by MASAKI, J.A.C.S., Vol. 90, Page 4508, (1968). Other methods of deprotection known from the literature can also be used.

Among the preferred groups are formyl, acetyl, ethoxycarbonyl, mesyl, trifluoroacetyl, chloroacetyl and trityl with trityl and chloroacetyl particularly preferred. The acid preferably used is trifluoroacetic acid.

Salification of the products can be carried out according to the usual methods. Salification can, for example, be obtained by reaction of a product in acid form or on a solvate, for example the ethanol solvate or a hydrate of this acid, with a mineral base such as sodium or potassium hydroxide, the carbonate or bicarbonate of sodium or potassium as well as the salts of mineral acids such as the tri-sodium phosphate or the salts of organic acids.

As organic acids, there can be mentioned, for example, the sodium salts of aliphatic carboxylic acids, saturated or unsaturated of 1 to 18 and preferably of 2 to 10 carbon atoms. These aliphatic acyls may be interrupted by one or more heteroatoms such as oxygen or sulfur or substituted by aryl such as phenyl, thienyl, furyl, or by one or more hydroxyl or by one or more halogens such as fluorine, chlorine or bromine, preferably chlorine, by one or more carboxylic or lower alkoxycarbonyl, preferably methoxycarbonyl, ethoxycarbonyl or propyloxycarbonyl, or by one or more aryloxy, preferably phenoxy.

Furthermore, the sufficiently soluble aromatic acids such as benzoic acids, for example, preferably substituted by lower alkyl can be used as organic acids. Examples of such organic acids are formic acid, acetic acid, acrylic acid, butyric acid, adipic acid, isobutyric acid, n-caproic acid, isocaproic acid, chloropropionic acid, crotonic acid, phenylacetic acid, 2-thienylacetic acid, 3-thienylacetic acid, 4-ethylphenylacetic acid, glutaric acid; also the monoethyl ester of adipic acid, and the following acids: hexanoic acid, heptanoic acid, decanoic acid, oleic acid, stearic acid, palmitic acid, 3-hydroxypropionic acid, 3-methoxypropionic acid, 3-methylthiobutyric acid, 4-chlorobutyric acid, 4-phenylbutyric acid, 3-phenoxybutyric acid, 4-ethylbenzoic acid, 1-propylbenzoic acid. It is, however, preferred to use as sodium salts, acetate or 2-ethyl hexanoate or diethyl acetate.

The salification can also be obtained by the action of an organic base such as triethylamine, diethylamine, trimethylamine, propylamine, N,N-dimethyl-ethanolamine, tris(hydroxymethyl)aminomethane, methylamine, ethanolamine, pyridine, picoline, dicyclohexylamine, morpholine and benzylamine. It can also be obtained by the action of arginine, lysine, procaine, histidine or N-methylglucamine. The salification is preferably carried out in a solvent or a mixture of solvents such as water, ethyl ether, methanol, ethanol or acetone.

The salts are obtained in amorphous or cyrstallized form depending on the reaction conditions employed. The crystallized salts are preferably prepared by making the free acids react with one of the salts of the aliphatic carboxylic acids mentioned above, preferably with sodium acetate. Salification of the products by mineral or organic acids is carried out under the usual conditions.

The optional esterification of the products is carried out under the standard conditions. In general, the operation is done by reacting the acid of formula I with a derivative of the formula:

Z-R$_s$ in which Z is hydroxyl or halogen such as chlorine, bromine or iodine, and R$_s$ is the ester group to be introduced, of which group a non-exhaustive list appears above. In certain cases, it can be of advantage to carry out an esterification on a product of which the amine is blocked before removing the protector group of the amine.

The possible resolution of the compounds of formula I can be effected with an optically active carboxylic acid or sulfonic organic acid such as tartaric acid dibenzoyltartaric acid, camphosulfonic acid or glutamic acid and the decomposition of the salt obtained being carried out with a mineral base such as sodium bicarbonate or an organic base such as a tertiary amine like triethylamine. Furthermore, there can also be used an optically active base.

The optional oxidation of the products of formula I can be carried out with oxygen, peroxides, hydroperoxides, peracids or hydrogen peroxide and the reaction is with advantage sensitized by light. These reagents can be mixed with organic or mineral acids and it is preferred to use m-chloroperbenzoic acid. The reaction conditions are known to an expert and such conditions are set out, for example in the French Pat. No. 2,387,234.

The novel antibiotic compositions of the invention are comprised of an antibiotically effective amount of at least one compound of formula I and their non-toxic, pharmaceutically acceptable acid addition salts and an inert pharmaceutical carrier or excipient. The compositions may be in the form of tablets, dragees, capsules, granules, suppositories, ointments, creams, gels and injectable solutions or suspensions.

Examples of suitable excipients are talc, gum arabic, lactose, starch, magnesium stearate, cocoa butter, aqueous or non-aqueous vehicles, fatty bodies of animal or vegetable origin, paraffin derivatives, glycols, various wetting, dispersing or emulsifying agents and preservaives.

The compositions possess a very good antibiotic activity on gram (+) bacteria such as the staphylococci, the streptococci and, notably, on the pencillin-resistant staphylococci. Their effectiveness on gram (−) bacteria, notably, on the coliform bacteria, klebsiella, salmonella and proteus is particularly remarkable. These properties render the compositions suitable for use as medicaments in the treatment of affections with sensitive germs, and, notably, those of staphylococcia such as staphylococcal septicemia, malignant facial or cutaneous staphylococcia, pyodermitis, septic or suppurating wounds, anthrax, phlegmons, erysipelas, acute primitive or post-influenzal staphylococcia, bronchopneumonia, pulmonary suppuration. The compositions can also be used as medicaments in the treatment of colibacilloses and associated infections, in infections by proteus, by klebsiella and by salmonella and in other affections caused by gram(−) bacteria and for sterilizing surgical instruments.

Particularly preferred are compounds of formula I' and especially those of formula I''. Specific preferred compositions contain as the active ingredient are of (6S)(7S)(Z) 4-[[[7-[[(2-amino-4-thiazolyl)-[(difluoromethoxy)-imino]-acetamido]-2-carboxy-8-oxo-4-thia-1-azabicyclo[4,2,0]oct-2-en-3-yl]-methyl]-thio]-1-methyl pyridinium, (6S)(7S)(Z) 4-[[[7-[[(2-amino-4-thiazolyl)-[(fluoromethoxy)-imino]-acetamido]-2-carboxy-8-oxo-4-thia-1-azabicyclo[4,2,0]oct-2-en-3-yl]-methyl]-thio]-1-methyl pyridinium, (6S)(7S)(Z) 2-[[[7-[[(2-amino-4-thiazolyl)-[(fluoromethoxy)-imino]-acetamido]-2-carboxy-8-oxo-4-thia-1-azabicyclo[4,2,0]oct-2-en-3-yl]-methyl]-thio]-1-methylpyridinium, (6S)(7S)(Z) 4-[[[7-[[2-(2-amino-4-thiazolyl)-2-(methoxy)-imino]-acetamido]-2-carboxy-8-oxo-4-thia-1-azabicyclo[4,2,0]oct-2-en-3-yl]-methyl]-thio]-1-ethyl-3-methyl pyridinium, (6S)(7S)(Z) 4-[[[7-[[2-amino-4-thiazolyl)-2-(methoxy)-imino]-acetamido]-2-carboxy-8-oxo-4-thia-1-azabicyclo[4,2,0]oct-2-en-3-yl]-methyl]-thio]-1,3-dimethyl pyridinium, (6S)(7S)(Z) 4-[[[7-[[(2-amino-4-thiazolyl) (methoxy)-imino]-acetamido]-2-carboxy-8-oxo-4-thia-1-azabicyclo[4,2,0]oct-2-en-3-yl]-methyl]-thio]-1-methylpyridinium, (6S)(7S)(Z) 4-[[[7-[[2-(2-amino-4-thiazolyl) (methoxy)-imino]-acetamido]-2-carboxy-8-oxo-4-thia-1-azabicyclo[4,2,0]oct-2-en-3-yl]-methyl]-thio]-1-methyl-5,6-dihydro pyridinium, in the form of an internal salt or of salts with mineral or organic acids.

The novel method of combatting bacterial infections in warm-blooded animals, including humans, comprises administering to warm-blooded animals an antibacterially effective amount of at least one compound of formula I and their non-toxic pharmaceutically effective acid addition salts. The compounds may be administered orally, rectally, parenterally or intramuscularly or topically to the skin or mucosa and the usual daily dose is depending on the condition being treated, the specific compound and the method of administration. For example, the compounds of Examples 2 and 3 may be administered intramuscularly at a dose of 6.5 to to 13.5 mg/kg. When A is a cleavable ester such as propionyloxymethyl, the compound is administered orally.

The starting products of formula VI' in which $n_1$ is 0 can be prepared by the process described in French Pat. No. 2,559,486. The products of formula VI' in which $n_1$ is 1 can be prepared by the following method.

A product of the formula

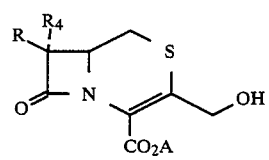

A in which R, R$_4$ and A have the preceding significance is reacted either with a halogenation agent or with a sulfonation agent then with triphenylphosphine, or a compound the formula P(OAlk)$_3$ in which Alk is alkyl of 1 to 4 carbon atoms to obtain either a product of the formula

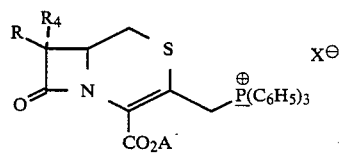

B in which R, R$_4$ and A have the preceding significance and X$^-$ represents the residue of an anion, or a product of the formula

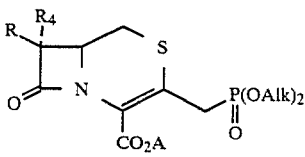

in which R, R<sub>4</sub>, A and Alk have the preceding significance, which product is reacted with a product of the formula

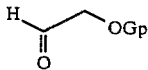

in which Gp is a protector group of hydroxyl to obtain a product of the formula

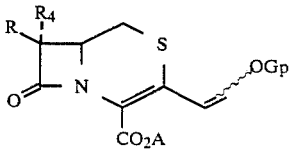

in the form of a mixture of E and Z isomers or in the form of the E or Z isomer, which product can be converted into a product of the formula

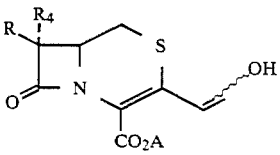

by elimination of Gp which can also be separated into E and Z isomers and which is converted into a product of formula VI' in which $n_1 = 1$ according to the usual methods. For example, to prepare the product of formula VI' in which X is iodine, a product of formula F is treated with tetrabutylammonium iodide in the presence of lutidine.

The products of formula VIII can be prepared by the usual methods starting with the corresponding $R_{AM}CO$ products.

In the following examples there are described several preferred embodiments to illustrate the invention. However, it should be understood that the invention is not intended to be limited to the specific embodiments.

Preparation of 1,1-dimethylethyl (6S,7S) (Z) 3-hydroxy 2(E) propenyl 7-[[2-(2-tritylamino 4-thiazolyl) 2-(methoxyimino) acetamido]8-oxo-4-thia-1-azabicyclo[4,2,0]oct-2-en-3yl]-2-carboxylate Step A:
[7-[(2-triphenylmethylaminothiazol-4-yl)-2(Z)-methoxyimino]-acetamido]-2-[(1,1-dimethyloxycarbonyl-8-oxo-4-thia-1-azabicyclo[4,2,0]oct-2-en-3-yl]-methyl-triphenyl phosphonium (6S,7S) chloride 2.182 g of 1,1-dimethylethyl (6S,7S) [7-[(2-triphenyl-methylaminothiazol-4-yl)-2-(Z)-methoxyimino]-acetamido]-3-chloromethyl-8-oxo-4-thia-1-azabicyclo[4,2,0]oct-2-en-2-carboxylate, and 1,679 g of triphenyl phosphine were dissolved in 24 ml of tetrahydrofuran was distilled off for 2 hours and the remainder was cooled, stirred for 26 hours at 20° C. and then chromatographed on silica. Elution with a mixture of dichloromethane and methanol (90/10) yielded 1.89 g of the product sought.

Step B: 1,1-dimethylethyl (6S,7S) 7-[2-(2-triphenylmethylaminothiazol-4-yl)-2(Z)-methoxyimino-acetamido]-3-[3-[(1,1-dimethylethyl)-dimethylsilyloxy]-propen-1-yl]-8-oxo-4-thia-1-azabicyclo[4,2,0]oct-2-en -2-carboxylate 1.89 g of (1,1-dimethyl)-ethyl 7-[(2-(2-triphenyl methylamino-thiazol-4-yl)-2(Z)-methoxyiminoacetamido]-3-methyltriphenyl-phosphonium-8-oxo-4-thia-1-azabicyclo [4,2,0]oct-2-en-2-carboxylate hydrochloride, 30 ml of dichloromethane, 0.68 ml of 2-[1,1-dimethyl-ethyl-dimethylsilyloxy]-acetaldehyde and 0.53 ml of triethylamine were mixed together and stirred at 20° C. for 14 hours. Then, the solution was chromatographed over silica and eluted with a mixture of dichloromethane and ethyl acetate (9/1) to obtain 1.305 g of the expected product containing a mixture of isomers E (2/3) and Z (1/3).

NMR Spectrum (CDCl3) 0.90–0.92 ppm SitBu; 1.50–1.53 ppm CO<sub>2</sub>tBu; 2.95–3.11 ppm 20 CH<sub>2</sub>S; 4.05 ppm OCH<sub>3</sub>; 4.31–4.37 ppm CH<sub>2</sub>O; 4.11 ppm H<sub>6</sub>; 5.4–5.5 ppm H; 5.75–5.87 ppm and 6.11–6.24 ppm Z (⅓); 6.17–6.34 ppm and 6.97–7.16 ppm E (⅔); 6.50–6.56 ppm H<sub>5</sub> thiazole syn; 7.34 ppm O<sub>3</sub>.

Step C: (1,1-dimethylethyl 7-[2-(2-triphenylmethylaminothiazol-4-yl)-2(Z)-methoxyimino-acetamido]-3-[3-hydroxypropen-1-(E)-yl]-8-oxo-4-thia-1-azabicyclo[4,2,0]oct-2-en-2-carboxylate, and (1,1-dimethylethyl) 7-[2-(2-triphenylmethylaminothiazol-4-yl)-2(Z)-methoxyimino-acetamido]-3-[3-hydroxypropen-1-(E)-yl]-8-oxo-4-thia-1-azabicyclo[4,2,0]oct-2-en-2-carboxylate 1.305 g of the product of Step B of Example 1 were dissolved in 15 ml of acetone and 2 ml of a normal aqueous solution of hydrochloric acid were added with stirring for 150 minutes, followed by concentration to dryness by distilling under reduced pressure. Bicarbonated water was added and extraction was done with dichloromethane. The extracts were concentrated to dryness by distilling under reduced pressure and the residue was chromatographed on silica. Elution with with a mixture of dichloromethane and ethyl acetate (1/1) yield 536 mg of isomer E and 369 mg of isomer Z of the expected product.

Isomer (E)

U.V.Spectrum.: (ethanol) Max. 231 nm $E^1_1 = 497$, $\epsilon = 32,200$; Inflexion 258 nm $E^1_1 = 290$; Inflexion 264 nm $E^1_1 = 264$; Inflexion 270 nm $E^1_1 = 240$; Max. 320 nm $E^1_1 = 245$, $\epsilon = 18,100$.

Isomer (Z)

U.V.Spectrum.: (ethanol) Inflexion 230 nm $E^1_1 = 411$; Inflexion 260 nm $E^1_1 = 220$; Inflexion 265 nm $E^1_1 = 198$; Inflexion 271 nm $E^1_1 = 176$; Max. 308 nm $E^1_1 = 194$, $\epsilon = 14,300$.

DETRITYLATION - DETERBUTYLATION

Under an inert atmosphere, 144 mg of the said product preceding and 1.8 ml of a 66% aqueous formic acid solution were mixed together and stirred at 60° C. for 90 minutes, then cooled. The insoluble matter formed was eliminated by filtering and washing with water. 2 ml of ethanol were added to the filtrate which was then concentrated to dryness by distilling under reduced pressure. 1 ml of water and 1 ml of ethanol were added to the residue, and after again concentrating to dryness, 5 ml of ethyl acetate were added to the residue, followed by concentration. Then, the precipitate formed was isolated by centrifuging and was washed and dried to obtain 125 mg of crude product to which were added 5 ml of trifluoroacetc acid and 50 μl of water. Then the mixture was stirred at 20° C. for 20 minutes and 5 ml of ether were added slowly with stirring. The precipitate formed was isolated by centrifuging, washed and dried to obtain 59 mg of the expected product.

U.V. Spectrum. (ethanol+0.1N HCl) Max. 218 nm $E^1_1=374$, $\epsilon=30,244$; Inflexion 247 nm $E^1_1=261$; Inflexion 260 nm $E^1_1=247$, $\epsilon=20,000$; Inflexion 278 nm $E^1_1=240$; Max. 317 nm $E^1_1=217$, $\epsilon=17,500$.

EXAMPLE 1

Iodide (60%), trifluoroacetate (40%) of
2-[3-[7-[[(2-amino-4-thiazolyl)-[(fluoromethyloxyimino]-acetamido]-2-carboxy
-8-oxo-4-thia-1-azabicyclo[4,2,0]oct-2-en-3-yl]-2(E)-propenyl]thio]-1-methyl pyridinium (trifluoroacetate)

(1) Hydroxyl-iodine exchange

Under an inert atmosphere, 200 mg of 1,1-dimethyl (6S,7S) (Z)-3-hydroxy-2(E)-propenyl-7-[[2-[2-triphenylmethylamino-4-thiazolyl]-[2-(fluoromethoxyimino]-acetamido]-8-oxo-4-thia-1-azabicyclo[4,2,-0]oct-2-en-3-yl]-2-carboxylate, 4 ml methylene chloride, 195 mg of tetra-butylammonium iodide and 123 μl of 2,6-lutidine were mixed together and then at −70° C. and over about 10 minutes, 1.8 ml of a 5% solution of trifluoromethane sulfonate in methylene chloride were introduced with stirring at −70° C. for 15 minutes, followed by concentration to dryness by distilling under reduced pressure first at −70° C. then at 20° C. The residue was chromatographed over silica and eluted with a mixture of methylene chloride and ethyl acetage (90/10) to obtain 170 mg of the expected product.

(2) Iodine-base exchange

Under an inert atmosphere, 170 mg of the said iodide derivative, 24 mg of 1-methyl-2-thio-pyridine, and 3 ml of acetonitrile were mixed together and stirred at 20° C. for 30 minutes, and concentrated to dryness by distilling under reduced pressure. The residue was chromatographed over silica under nitrogen pressure and eluted with a mixture of methylene chloride and methanol (90/10) to obtain 114 mg of the expected product.

The 1,1-dimethylethyl-(6S,7S)(Z) 3-hydroxy-2(E)-propenyl 7-[[[2-(2-tritylamino 4-thiazolyl)-2-(difluoromethoxyimino) acetamido]-8-oxo-4-thia-1-azabicyclo[4,2,0]oct-2-en-3-yl]-2-carboxylate used at the start of the example was prepared in a similar manner to that described below for the "methoxyimino" starting from the corresponding derivative.

EXAMPLE 2

(6S)(7S)(Z) trifluoroacetate of
4-[[[7-[(2-amino-4-thiazolyl)[(difluoromethoxyimino]-acetamido]-2-carboxy-8-oxo-4-thia-1-azabicyclo[4,2,-0]oct-2-en-3-yl]-methyl thio]-1-methyl pyridinium (trifluoroacetate)

Step A:
7-(2-triphenylmethylamino-4-thiazolyl)-2-(methoxyimino)-acetamido]-2-tertbutoxycarbonyl-8-oxo-4-thia-1-azabicyclo[4,2,0]oct-2-en-3-yl]-iodomethyl 3 g of 2-[7-(2-triphenylmethylamino-4-thiazolyl)-2-(methoxyimino)-acetamido]-2-tertbutoxycarbonyl-8-oxo-4-thia -1-azabicyclo[4,2,0]oct-2-en-3-yl]-methyl]-hydroxy were dissolved in 30 ml of methylene chloride and 2.021 g of tetrabutylammonium iodide and 1.96 ml of 2,6-lutidine were added. After cooling to −70° C., 8.7 ml of a solution of trifluoromethyl sulfonic anhydride titrating 1 ml for 10 ml were introduced. After stirring for 15 minutes at −70° C., the temperature was brought to 0° C. and the reaction mixture was poured into water, decanted, extracted with methylene chloride and concentrated to dryness by distilling under reduced pressure. The residue was dissolved in ethyl acetate and 10 ml of a 0.2N aqueous solution of sodium thio-sulfate were added with stirring. After decanting and extracting with ethyl acetate, the extracts were concentrated to dryness by distilling under reduced pressure. The residue was triturated with isopropylic ether and then concentrated to dryness to obtain 2.400 g of the expected product.

Step B: (6S)(7S)(Z) trifluoroacetate of
4-[[[7-[(2-amino-4-thiazolyl)-[(difluoromethoxy)-imino]-acetamido]-2-carboxy-8-oxo-4-thia-1-azabicyclo[4,2,-0]oct-2-en-3-yl]-methyl]-thio]-1-methyl pyridinium(trifluoroacetate)

(1) Condensation with the base

Under an inert atmosphere, 150 mg of 3-iodomethyl of 1,1-dimethyl-ethyl (6S)(7S)(Z) 7-[3-[7-[2-triphenylmethylamino-4-thiazolyl][(difluoromethyloxy)-imino]-acetamido]-8-oxo-4-thia -1-azabicyclo[4,2,0]oct-2-en-3-yl]-2-carboxylate (prepared like the methoxyimino described above), 33 mg of 4-thio-1-methylpyridine, and 2 ml of acetonitrile were mixed together, stirred at 20° C. for one hour and then concentrated to dryness by distilling under reduced pressure. The residue was chromatographed on silica under nitrogen pressure and eluted with a mixture of methylene chloride and methanol (90/10) to obtain 72 mg of the expected product.

(2) Detritylation, deterbutylation

Under an inert atmosphere, 72 mg of the said product, 0.3 ml of trifluoroacetic acid and 30 μl of water were mixed together and stirred at 20° C. for 2 hours. 3 ml of ether were added slowly, and after stirring the precipitate formed was isolated by centrifuging, washed, dried to obtain 45 mg of the expected product.

U.V. Spectrum. (ethanol) Max. 225 nm $E^1_1=375$, $\epsilon=29,900$; Max. 307 nm $E^1_1=353$, $\epsilon=28,200$.

U.V. Spectrum, (ethanol+0.1N HCl) Max. 223 nm $E^1_1=296$, $\epsilon=23,600$; Max. 257 nm $E^1_1=195$, $\epsilon=15,600$; Max. 302 nm $E^1_1=375$, $\epsilon=29,900$.

EXAMPLE 3

(6S)(7S)(Z) trifluoroacetate of 4-[[7-[[(2-amino-4-thiazolyl)[(fluoromethoxy)-imino]-acetamido]-2-carboxy-8-oxo-4-thia-1-azabicyclo[4,2,-0]oct-2-en-3-yl]-methyl]-thio]-1-methyl pyridinium (trifluoroacetate)

(1) Condensation with the base

Under an inert atmosphere, 150 mg of 3-iodomethyl of 1,1-dimethyl-ethyl (6S)(7S)(Z) 7-[3-[7-[2-triphenyl-methylamino-4-thiazolyl]-[(2-fluoromethoxy)-imino]acetamido]-8-oxo-4-thia-1-azabicyclo[4,2,0]oct-2-en-3-yl]-2-carboxylate (prepared like the methoxyimino), 33 mg of 4-thio-1-methyl-pyridine, and 2 ml of acetonitrile were mixed together, stirred at 20° C. for one hour and then concentrated to dryness by distilling under reduced pressure. The residue was chromatographed on silica and eluted with a mixture of methylene chloride and methanol (96/4) to obtain 110 mg of the expected product.

(2) Detritylation, deterbutylation.

Under an inert atmosphere, 110 mg of the said product, 0.440 ml of trifluoroacetic acid and 44 µl of water were mixed together and stirred at 20° C. for 2 hours. 10 ml of ether were added slowly, and after stirring, the precipitate formed was isolated by centrifuging, washed and dried to obtain 64 mg of the expected product.

U.V. Spectrum, (ethanol+0.1N HCl) Max. 224 nm $E^1_1=316$, $\epsilon=24,700$; Inflexion 260 nm $E^1_1=213$; Max. 303 nm $E^1_1=379$, $\epsilon=29,600$.

EXAMPLE 4

Internal salt of (6R,S) (7R,S)(Z) of 2-[[-7-[[2-amino-4-thiazolyl)-2-(methoxyimino)-acetamido]-2-carboxy-8-oxo-4-thia-1-azabicyclo[4,2,-0]oct-2-en-3-yl]-methyl]-thio]-1-methyl pyridinium

Step A: 4,6-diphenyl-2H-pyran-2-one

Under inert atmosphere, 60 g of ethyl benzoylacetate and 33 ml of concentrated sulfuric acid were mixed together and stirred at 20° C. under inert atmosphere for 2 weeks. Then, the reaction mixture was poured on to ice and was extracted with ether. The extracts were washed with water and concentrated to dryness by distilling under reduced pressure. 30 ml of ether were added to the residue which was then cooled to 0° C., stirred, and the precipitate formed was separated off, washed and dried. The mother liquors were taken to dryness to crystallize out. 10 ml of ether were added to the residue and the precipitate formed was separated, washed with ether and dried. The first and second lots were combined to obtain 11 g of the product sought melting at 138° C.

Step B: 4,6-diphenyl-2H-pyran-2-thione

Under an inert atmosphere, 2.1 g of the product of Step A 45 ml of benzene and 7.5 g of phosphorus pentasulfide were mixed together and refluxed under inert atmosphere for 5 hours. Then the supernatant solution was decanted hot and concentrated to dryness by distilling under reduced pressure. This operation was repeated hot on the reaction medium four times, each time with 30 ml of benzene. The concentrates were put together and dried under a good vacuum to obtain 3 g of product which was chromatographed on silica and eluted with methylene chloride to obtain 2 g of the product sought melting at 122°-123° C.

Step C: 1-(2-hydroxyethyl)-4,6-diphenylpyridin-2-thione

Under nitrogen, 2 g of the product of Step B and 40 ml of methanol were mixed together and heated to reflux. Then, in one lot, a solution of 560 mg of ethanolamine in 2 ml of methanol was added and reflux was maintained for 5 hours, followed by cooling and concentrating to dryness by distilling under reduced pressure. The 2.4 g of residue were chromatographed on silica and eluted with a mixture of methylene chloride and ethyl acetate (80/20) to obtain 1.6 g of the product sought.

U.V. Spectrum. (ethanol) Max. 278 nm $E^1_1=885$, $\epsilon=27,200$; Max. 390 nm $E^1_1=263$, $\epsilon=8,100$.

Step D:
7-[[[2-[(2-tritylaminothiazol-4-yl)-2-(methoxyimino)acetamido]-8-oxo-2-(1,1-dimethyl)-ethyloxycarbonyl-4-thia -1-azabicyclo[4,2,0]oct-2-en-3-yl]-methyl]-thio]-1-methyl pyridinium (6 R,S) (7 R,S)(Z) iodide (1) 1,1-dimethyl-ethyl (6 R,S)(7 R,S)(Z) 3-thiolmethyl-7-[2-(2-triphenylmethylamino-4-thiazolyl)-(methoxy)-imino]-acetamido]-8-oxo-4-thia-1-azabicyclo[4,2,-0]oct-2-en-3-yl]-2-carboxylate, not isolated.

Under an inert atmosphere, 368 mg of the product of Step C and 50 ml of acetonitrile were mixed together and stirred, and 984 mg of 1,1-dimethylethyl (6 R,S)(7R,S)(Z) 3-iodomethyl 7-[2-[2-(triphenyl-methylamino-4-thiazolyl)(methoxy)-imino]-acetamido]-8-oxo-4-thia-1-azabicyclo[4,2,0]oct-2-en-3-yl]-2-carboxylate were added all at once with stirring for 1 hour at 20° C. and the thiol solution sought was obtained.

(2) Iodide of 7-[2-[(2-tritylaminothiazol-4-yl)-2-(methoxyimino)-acetamido]-8-oxo-2-(1,1-dimethyl)-ethyloxycarbonyl-4-thia-1-azabicyclo[4,2,0]oct-2-en-3-yl]-methyl]-thio]-1-methyl pyridinium (6 R,S)(7R,S)(Z).

To the solution of thiol there were added in one lot 306 mg of 2-chloro-1-methyl pyridinium iodide, then 0.2 ml of diisopropylamine, and after stirring for 1 hour at 20° C., the mixture was concentrated to dryness by distilling under reduced pressure. The residue was chromatographed on silica and eluted with a mixture of methylene chloride and methanol (9/1). At the moment of dissolving and putting on the column, a considerable crystallization of 2,3-dihydro-5,7-diphenyloxazolo[3,2-a] pyridinium was noted, and the precipitate formed was separated off. The mother liquors were chromatographed under the previously indicated conditions to obtain 720 mg of the product sought.

Step E: Internal salt of
2-[[[7-[[2-(2-amino-4-thiazolyl)-2-(methoxyimino)-acetamido]-2-carboxy-8-oxo-4-thia-1-azabicyclo [4,2,0]oct-2-en-3-yl]-methyl]-thio]-1-methyl pyridinium (6 R,S) (7 R,S)(Z)

(1) Detritylation and deterbutylation to obtain a 1:1 mixture of the iodide and the trifluoroacetate of 2-[[7-[[2-(2-amino-4-thiazolyl)-2-(methoxyimino)-acetamido]-2-carboxy-8-oxo-4-thia -1-azabicyclo[4,2,0]oct-2-en-3-yl]-methyl]-thio]-1-methyl pyridinium (6 R,S)(7R,S)(Z).

Under an inert atmosphere, 2 ml of trifluoroacetic acid with 10% of water were added to 460 mg of the product of Step D with stirring at 20° C. for 1 hour and 20 mg of ether were added dropwise with stirring at 20°

C. for one hour. The precipitate formed was separated off, washed and dried to obtain 254 mg of the product sought melting at 150° C. not very pure.

(2) Obtaining the internal salt

An H.P.L.C. chromatography was carried out on grafted RP 18 silica. After dissolving in a mixture of 1.5 ml of triethylamine carbonate and 1.5 ml of acetonitrile, elution was done with successive mixtures of distilled water containing from 5 to 20% acetonitrile. The majority of the product was collected in the fraction eluted by the distilled water with 10% of acetonitrile. After lyophilysing, 90 mg of the internal salt sought melting about 250° C. (decomposes) were obtained.

U.V. Spectrum. (ethanol+0.1N HCl) Inflexion 225 nm $E^1_1=296$; Max. 258 nm $E^1_1=304$, $\epsilon=15,800$; Inflexion 288 nm $E^1_1=304$; Max. 295 nm $E^1_1=307$, $\epsilon=16,000$; Max. 310 nm, $\epsilon=15,600$.

EXAMPLE 5

Internal salt of 2-[[7-[[2-(2-amino-4-thiazolyl)-2-(methoxyimino)-acetamido]-2-carboxy-8-oxo-4-thia-1-azabicyclo[4,2,-0]oct-2-en-3-yl]-methyl]-thio]-1-methyl pyridinium (6S)(7S)(Z)

Step A: 1-methyl-2-pyridine thione

Under an inert atmosphere, 1 g of 1-methyl-2-pyridine and 20 ml of benzene were mixed together and then 2 g of 2,4-bis-(4-methoxyphenyl)-2,4-dithioxo-1,3,2,4-dithia-diphosphetane (Lawesson's reagent) were added all at once with vigorous stirring followed by stirring for 2 hours at reflux. After cooling, filtering, and washing with benzene, the benzene filtrate was concentrated to dryness by distilling under reduced pressure. The 2.8 g of residue were chromatographed on silica and eluted with a mixture of methylene chloride and ethyl acetate (8/2) to obtain 900 mg of the product sought melting at 98° C.

U.V. Spectrum. (ethanol) Inflexion 220 nm $E^1_1=440$; Max. 284 nm $E^1_1=1100$ $\epsilon=13,800$; Max. 354 nm $E^1_1=569$ $\epsilon=7,100$.

Step B: (1,1-dimethyl)-ethyl (6S)(7S)(Z)-3-iodomethyl-7-[2-[2-(triphenylmethyl)-amino-4-thiazolyl]-2-(methoxyimino) -acetamido]-8-oxo-4-thia-1-azabicyclo[4,2,0]oct-2-en-2-carboxylate 2 g of (1,1-dimethyl)-ethyl (6S)(7S)(Z)-3-hydroxymethyl-7-[2-[2-(triphenylmethyl)-amino-4-thiazolyl]-2-(methoxyimino)-acetamido]-8-oxo-4-thia-1-azabicyclo[4,2,0]oct-2-en-2-carboxylate, 20 ml of methylene chloride, 1.3 g of tetrabutylammonium iodide and 1.3 ml of 2,6-lutidine were mixed together, and over about 15 minutes at −70° C., 9 ml of a 10% solution of trifluoromethane sulfonic anhydride in methylene chloride were added. After plunging for 15 minutes in an ice bath, 200 ml of a 0.1N aqueous solution of hydrochloric acid were added with stirring followed by decanting and extraction with methylene chloride. The extracts were concentrated to dryness by distilling under reduced pressure and the 4.36 g of residue were chromatographed on silica and eluted by a gradient of 1 to 10% of ethyl acetate in methylene chloride to obtain 1.324 g of the product sought with a specific rotation of $[\alpha]_D=+13°$ (c=0.5% in chloroform) and melting at 150° C. not very pure.

Step C: Iodide of 7-[[2-[(2-tritylaminothiazol-4-yl)-2-(methoxyimino)-acetamido]-8-oxo-2-(1,1-dimethyl)-ethoxycarbonyl-4-thia-1-azabicyclo[4,2,0]oct-2-en-3-yl]-methyl]-thio]-1-methyl pyridinium (6S)(7S)(Z)

Under an inert atmosphere, 820 mg of the iodized derivative of Step B and 20 ml of acetonitrile were mixed together, and 125 mg of N-methyl-2-pyridine thione of Step A were added all at once with stirring for 1 hour at 20° C. The mixture was concentrated to dryness by distilling under reduced pressure, then dried under a good vacuum, and the 930 mg of residue were chromatographed on silica and eluted with a mixture of methylene chloride and methanol (9/1) to obtain 800 mg of the desired product with a specific rotation of $[\alpha]_D=-16°$ (c=0.7% in chloroform).

Step D: Internal salt of 2-[[[7-[2-(2-amino-4-thiazolyl)-2-(methoxyimino)-acetamido]-2-carboxy-8-oxo-4-thia-1-azabicyclo[4,2,-0]oct-2-en-3-yl]-methyl]-thio]-1-methyl pyridinium (6S)(7)(Z).

(1) Deterbutylation, detritylation to obtain the 1:1 mixture of the iodide and the trifluoroacetate of 2-[[[7-[[2-(2-amino-4-thiazolyl)-2-(methoxyimino)-acetamido]-2-carboxy-8-oxo-4-thia-1-azabicyclo[4,2,0]oct-2-en-3-yl]-methyl]-thio]-1-methyl pyridinium (6S)(7S)(Z).

At 0° C., 700 mg of the product of Step C and 3 ml of trifluoroacetic acid with 10% of water were mixed together and stirred for 1 hour at 20° C. 20 ml of ether were added dropwise with stirring at 20° C. for one hour until complete concretion of the precipitate. The insoluble matter was separated off, washed and dried under vacuum to obtain 580 mg of the product sought melting at 150°-160° C. with decomposition.

(2) Obtaining the internal salt.

580 mg of the said product, 3 ml of acetonitrile and 3 ml of triethylamine carbonate were mixed together, and the solution obtained was fixed on a H.P.L.C. column and eluted with a mixture of water and acetonitrile at gradients variable from 5 to 10% to obtain 100 mg of the product sought melting at 190°-200° C. with decomposition and having a specific rotation of $[\alpha]_D=+28°$ (c=0.4% in water with a few drops of 0.1N HCl).

U.V. Spectrum. (ethanol+0.1N HCl) Inflexion 240 nm $E^1_1=344$; Inflexion 265 nm $E^1_1=337$; Max. 284 nm $E^1_1=374$, $\epsilon=19,500$; Inflexion 290 nm $E^1_1=365$; Inflexion 307 nm $E^1_1=306$; Inflexion 318 nm $E^1_1=276$.

EXAMPLE 6

7-[2-(2-amino-4-thiazolyl)-2-(methoxyimino)-acetamido]-3-[(1-oxide-pyridin-2-yl)-thiomethyl]-8-oxo-4-thia-1-azabicyclo[4,2,0]oct-2-en-2-carboxylic acid (6R,S)(7R,S)(Z)

Step A: 1,1-dimethylethyl (6 R,S)(7 R,S)(Z) 7-[2-(2-triphenylmethylamino-4-thiazolyl)-2-methoxyimino-acetamido]-3-[(1-oxidepyridin-2-yl)-thiomethyl]-8-oxo-4-thia-1-azabicyclo[4,2,0]oct-2-en-2-carboxylate 330 mg of 1,1-dimethylethyl (6 R,S)(7 R,S)(Z) 3-iodomethyl-[[[7-[2-(2-triphenylmethyl)-amino-4-thiazolyl)-2-methoxyimino]-acetamido]-8-oxo-4-thia-1-azabicyclo[4,2,0]oct-2-en-2-carboxylate, 1.3 ml of acetonitrile, 61 mg of 2-mercaptopyridine-N-oxide and 67 mg of potassium carbonate were mixed together and stirred at 20° C. for 90 minutes. After concentrating to dryness by distilling under reduced pressure, the residue was chromatographed on silica and eluted with a mixture of methylene chloride and acetone (6/4) to obtain 212 mg of the product sought.

Step B:
7-[2-(2-amino-4-thiazolyl)-2-(methoxyimino)-acetamido]-3-[(1-oxide-pyridin-2-yl)-thiomethyl]-8-oxo-4-thia-1-azabicyclo [4,2,0]oct-2-en-2-carboxylic acid (6 R,S)(7 R,S)(Z)

200 mg of the product of Step A and 2 ml of formic acid with 33% of water were mixed together and stirred at 20° C. for 1 hour, then for 5 hours at 50° C., after which it was cooled and the triphenylmethyl carbinol formed was eliminated by filtering. The filtrate was concentrated to dryness by distilling under reduced pressure and ethyl acetate was added followed by concentrating to dryness again and this operation was repeated many times. Ethyl acetate was added and the precipitate was stirred in ethyl acetate, then separated, washed and dried to obtain 114 mg of the product sought melting at 220° C.

U.V. Spectrum. (ethanol) Max. 240 nm $E^1_1=725$, $\epsilon=37,900$; Max. 300 nm $E^1_1=311$, $\epsilon=16,300$; Inflexion 224 and 270 nm.

U.V. Spectrum. (ethanol+0.1N HCl) Max. 242 nm $E^1_1=645$, $\epsilon=33,700$; Inflexion 264 nm $E^1_1=405$; Inflexion 280 nm $E^1_1=371$; Inflexion 290 nm $E^1_1=340$; Inflexion 307 nm $E^1_1=288$.

EXAMPLE 7

Iodide of 2-[[[7-[2-(2-amino-4-thiazolyl)-2-(methoxyimino)acetamido]-2-carboxy-8-oxo-4-thia-1-azabicyclo[4,2,0]oct-2-en-3-yl]-methyl]-thio]-1-methyl-3-methoxy pyridinium (6 R,S) (7 R,S)(Z)

Step A: N-methyl-3-methoxy-2-thiopyridone

Under an inert atmosphere, 2.1 g of N-methyl-3-methoxy-2-pyridone and 50 ml of benzene were mixed together, and 3 g of 2,4-bis-(4-methoxyphenyl)-2,4-dithioxo-1,3,2,4-dithiadiphosphetane (Lawesson's reagent) were added all at once with stirring at reflux for 3 hours. After cooling and concentrating to dryness by distilling under reduced pressure, the residue was chromatographed on silica and eluted with a mixture of methylene chloride and methanol (9/1) to obtain 1.2 g of the product sought melting at 130°–132° C.

Step B: Iodide of 7-[[[2-[(2-tritylaminothiazol-4-yl)-2-(methoxyimino)-acetamido-8-oxo-2-(1,1-dimethylethyloxycarbonyl-4-thia-1-aza bicyclo[4,2,0]oct-2-en-3-yl-methyl]-thio]-1-methyl-3-methoxy pyridinium (6 R,S) (7 R,S)(Z)

Under an inert atmosphere, 164 mg of 1,1-dimethylethyl (6 R,S)(7 R,S)(Z) 3-iodomethyl-7-[2-[2-(triphenylmethylamino-4-thiazolyl)-[(methoxy)imino]-acetamido]-8-oxo-4-thia-1-azabicyclo [4,2,0]oct-2-en-3-yl]-2-carboxylate and 5 ml of acetonitrile were mixed together, and 31 mg of the product of Step A were added all at once with stirring at 20° C. for 2 hours. After concentrating to dryness by distilling under reduced pressure the residue was chromatographied on silica and eluted with a mixture of methylene chloride and methanol (9/1) to obtain 145 mg of the product sought melting at 170°–180° C. (with decomposition).

Step C: Iodide of 2-[[7-[2-(2-amino-4-thiazolyl)-2-(methoxyimino)-acetamido]-2-carboxy-8-oxo-4-thia-1-azabicyclo[4,2,0]oct-2-en-3-yl]-methyl]-thio]-1-methyl-3-methoxy pyridinium (6 R,S)(7 R,S)(Z).

Under an inert atmosphere, 110 mg of the product of Step B were mixed together with 2 ml of a 66% aqueous solution of formic acid with stirring for 150 minutes at 60° C. After cooling, the triphenylcarbonyl formed was filtered off. The filtrate was concentrated to dryness by distilling under reduced pressure and ethyl acetate was added, followed by concentration to dryness again and the same operation was repeated several times. Then, ethyl acetate was added and the precipitate formed was separated, washed with ether and dried under a good vacuum to obtain 75 mg of the product sought melting at 190°–200° C. (with decomposition).

U.V. Spectrum. (ethanol) Max. 215 nm $E^1_1=555$, $\epsilon=37,700$; Max. 294 nm $E^1_1=232$, $\epsilon=15,700$; Inflexion 335 nm $E^1_1=117$, $\epsilon=7,900$.

U.V. Spectrum. (ethanol+0.1N HCl) Max. 214 nm $E^1_1=497$, $\epsilon=33,700$; Inflexion 263 nm $E^1_1=244$; Max. 285 nm $E^1_1=270$, $\epsilon=18,300$; Max. 338 nm $E^1_1=138$, $\epsilon=9,350$.

EXAMPLE 8

Internal salt of 2-[[[7-[2-(2-amino-4-thiazolyl)-2-methoxyimino]-acetamido]-2-carboxy-8-oxo-4-thia-1-azabicyclo-[4,2,0]oct-2-en-3-yl]-methyl]-thio]-1-methyl quinolinium (6S)(7S)(Z)

Step A: 1-methyl-quinoline-2-thione

Under inert atmosphere, 1 g of 1-methyl-quinolin-2-one and 25 ml of benzene were mixed together and then 1.27 g of 2,4-bis-(4-methoxyphenyl)-2,4-dithioxo-1,3,2,4-dithiadiphos phetane (Laweseeon's reagent) were added all at once. After stirring at reflux for 1 hour, cooling, eliminating the solvent by distilling under reduced pressure and drying under a good vacuum and chromatographing, the residue was chromatographed on silica and eluted with a mixture of methylene chloride and ethyl acetate (1/1) to obtain 1 g of the product sought melting at 114° C.

Step B: Iodide of 7-[[[2-[(2-tritylaminothiazol-4-yl)-2-methoxyimino)-acetamido]-8-oxo-2-(1,1-dimethyl)-ethoxycarbonyl-4-thia-1-azabicyclo[4,2,0]oct-2-en-3-yl]-methyl]-thio]-1-methyl quinolinium (6S)(7S)(Z)

Under an inert atmosphere, 328 mg of 1,1-dimethylethyl (6S)(7S)(Z) 3-iodomethyl-7-[2-[2-triphenylmethyl)-amino-4-thiazolol][(methoxy)-imino]-acetamido]-8-oxo-4-thia-1-azabicyclo[4,2,0]oct-2-en-3-yl]-2-carboxylate and 10 ml of acetonitrile were mixed together and then at 20° C., 70 mg of the product of Step A were added all at once with stirring at 20° C. for one hour. The acetonitrile was distilled off under reduced pressure, and after drying under good vacuum, 400 mg of the product sought were obtained, which was used as is for the next step.

Step C: Internal salt of 2-[[[7-[2-(2-amino-4-thiazolyl)-2-methoxyimino]-acetamido]-2-carboxy-8-oxo-4-thia-1-azabicyclo [4,2,0]oct-2-en-3-yl]-methyl]-thio]-1-methyl quinolinium (6S)(7S)(Z)

(1) Detritylation, detertbutylation

Under an inert atmosphere, 360 mg of the compound of Step B and 6 ml of a 60% aqueous solution of formic acid were mixed together and stirred for 3 hours at 60° C. and then cooled, and the triphenyl carbinol formed was eliminated by filtering. The remainder was concentrated to dryness by distilling under reduced pressure to obtain 300 mg of the incompletely deblocked product, which was introduced into 1 ml of trifluoroacetic acid with 10% of water. The mixture was stirred for 1 hour at 20° C. and then 15 ml of ether were added dropwise with stirring, and the precipitate formed was separated, washed and dried to obtain 260 mg of the product sought, detritylated and detertbutylated.

(2) Internal salt

Under an inert atmosphere, 1.5 ml of triethylamine carbonate and 1.5 ml of acetonitrile were mixed together to obtain a solution which was injected in a column of 65 ml by 25 ml diameter filled with Lynchoprop RP 18, 5/20 microns. After eluting with a variable gradient mixture of water-acetonitrile, the peaks at 5% to 10% (impurities) were isolate. Then, elution was done with water with 15% acetonitrile and with water with 20% of acetonitrile and after lyophilizing, 49 mg of the expected product melting at 190°-200° C. were obtained.

U.V. Spectrum. (ethanol) Max. 216 nm $E^1_1=930$, $\epsilon=53,100$; Inflexion 231 nm $E^1_1=402$; Inflexion 236 nm $E^1_1=382$; Max. 276 nm $E^1_1=489$, $\epsilon=27,900$; Inflexion 292 nm $E^1_1=319$, Inflexion 302 nm $E^1_1=247$; Max. 376 nm $E^1_1=186$, $\epsilon=10,600$.

U.V. Spectrum (ethanol+0.1N HCl) Max. 216 nm $E^1_1=877$, $\epsilon=50,100$; Max. 275 nm $E^1_1=588$, $\epsilon=33,600$; Max. 375 nm $E^1_1=189$, $\epsilon=10,800$. Inflexions at 231, 238, 292 and 306 nm.

EXAMPLE 9

Trifluoroacetate of 4-[[7-[2-(2-amino-4-thiazolyl)-2-(methoxyimino)-acetamido]-2-carboxy-8-oxo-4-thia-1-azabicyclo[4,2,-0]oc-2-en-3-yl]-methyl]-thio]-1-methyl quinolinium trifluoro acetate, (6S)(7)(Z)

Step A: 1-methyl-quinolin-4-thione

Under an inert atmosphere, 1 g of 1-methyl-4-quinolone was dissolved in 20 ml of benzene and then under bigorous stirring, 1.27 g of 2,4-bis-(4-methoxyphenyl)-2,4-dithioxo-1,3,2,4-dithiadiphosphetane (Lawesson's reagent) was added all at once with stirring for 1 hour at reflux. After cooling and concentrating to dryness by distilling under reduced pressure, the 2.5 g of residue were chromatographed on silica and eluted with a mixture of methyl chloride and methanol (9/1) to obtain 910 mg of the expected product melting at 208°-210° C.

Step B: Iodide of 7-[[4-[2-tritylaminothiazol-4-yl)-2-(methoxyimino)-acetamido]-8-oxo-2-(1,1-dimethyl)-ethoxycarbonyl-4-thia -1-azabicyclo[4,2,0]oct-2-en-3-yl]-methyl-thio]-1-methyl quinolinium (6S)(7S)(Z)

Under an atmosphere of nitrogen, 328 mg of (1,1-dimethyl) ethyl (6S)(7S)(Z) 3-iodomethyl-7-[2-[(trityl-phenylmethyl)-amino-4-thiazolyl]-2-methoxyimino]-acetamido]-8-oxo-4-thia-1-azabicyclo [4,2,0]oct-2-en-2-carboxylate and 10 ml of acetonitrile were mixed together and then at 20° C., 70 mg of 1-methyl quinolin-4-thione were added all at once with stirring at 20° C. for 30 minutes, followed by concentrating to dryness by distilling under reduced pressure. The 405 mg of residue were triturated with 5 ml of ether while stirring for 30 minutes at 20° C. Then the precipitate formed was separated, washed and dried to obtain 390 mg of the expected product melting about 210° C. with decomposition and having a specific rotation $[\alpha]_D = -76°$ (c=0.5% in chloroform).

Step C: Trifluoroacetate of 4-[[7-[2-(2-amino-4-thiazolyl)-2-methoxyimino]-acetamido]-2-carboxy-8-oxo-4-thia-1-azabicyclo [4,2,0]oct-2-en-3-yl]-methyl]-thio]-1-methyl quinolinium trifluoroacetate, (6S)(7S)(Z)

Under an inert atmosphere, 340 mg of the product of Step B and 1.5 ml of trifluoroacetic acid with 10% of water were mixed together at 0° C. and vigourously stirred at 20° C. for 45 minutes. 15 ml of ether were added dropwise and was stirred at 20° C. for 1 hour. The precipitate formed was separated, washed, and dried under vacuum to obtain 258 mg of the expected product melting at about 210° C. with decomposition and having a specific rotation $[\alpha]_D = -43°$ (c=0.5% in methanol).

EXAMPLE 10

Internal salt of 2-[[[7-](2-amino4thiazolyl)-(methoxyimino)-acetamido]-2-carboxy-8-oxo-4-thia-1-azabicyclo[4,2,0]oct-2-en-3-yl]-methyl]-thio]-1-ethyl pyridinium (6S)(7S)(Z)

Step A: 1-ethyl-2-pyridine-thione

Under an inert atmosphere, 1.23 g of 1-ethyl-2-pyridone and 25 ml of benzene were mixed together and then under vigorous stirring, 2.02 g of 2,4-bis-(4-methoxyphenyl)-2,4-dithioxo1,3,2,4-dithiadiphosphetane (Lawesson's reagent) were added all at once with stirring at reflux for 2 hours. After cooling and filtering, the filtrate was taken to dryness by distilling under reduced pressure, and the 3.8 g of residue were chromatographed on silica and eluted with a mixture of methylene chloride and ethyl acetate (8/2) to obtain 1.3 g of the expected product melting at about 50° C.

Step B: Iodide of 2-[[[2-[(2-tritylamino-4-thiazolyl)(methoxyimino]-acetamido]-8-oxo-2-(1,1-dimethyl)-ethoxycarbonyl-4-thia -1-azabicyclo[4,2,0]oct-2-en-3-yl]-methyl]-thio]-1-ethyl pyridinium (6S)(7S)(Z)

Under an inert atmosphere, 350 mg of (1,1-dimethyl)-ethyl (6S)(7S)(Z) 3-iodomethyl-7-[2-[2-(triphenylmethyl)-amino-4-thiazolyl]-2-methoxyimino]-acetamido]-8-oxo-4-thia-1-azabicyclo [4,2,0]oct-2-en-2-carboxylate, 3.5 ml of acetonitrile and 71 mg of the product of Step A were mixed together and stirred at 20° C. for 30 minutes, followed by concentrating to dryness by distilling under reduced pressure. The 450 mg of residue were chromatographed on silica and eluted with a mixture of methylene chloride and methanol (9/1) to obtain 347 mg of the product sought.

Step C: Internal salt of 2-[[[7-[2-(2-amino-4-thiazolyl)-methoxyimino)-acetamido]-2-carboxy-8-oxo-4-thia-1-azabicyclo [4,2,0]oct-2-en-3-yl]-methyl]-thio]-1-ethyl pyridinium (6S)(7S)(Z)

(1) Detertbutylation and detritylation 330 mg of the product of Step B were mixed together with 1.6 ml f trifluoroacetic acid with 10% of water and stirred at 20° C. for 50 minutes. 7 ml of ether were introduced slowly with stirring for 2 hours and then the precipitate formed was separated, washed and dried to obtain 250 mg of the deblocked product melting at 200° C.

(2) Obtaining the internal salt 240 mg of the said product were dissolved in 1.2 ml of acetonitrile and 1.2 ml of a 1M solution of triethylamine carbonate and the solution was fixed on a silica column (length 65 ml, diameter 2.7 cm) and was eluted successively with 1 liter of the following mixture:

| Acetonitrile % | Water |
|---|---|
| 5 | 95 |
| 10 | 90 |
| 15 | 85 |
| 20 | 80 |

The fractions containing the expected product were collected and lyophilized to obtain 115 mg of the product sought melting at 200° C.

U.V. Spectrum. (ethanol) Inflexion 224 nm $E^1_1=408$; Inflexion 234 nm $E^1_1=376$; Max. 296 nm $E^1_1=326$.

U.V. Spectrum. (ethanol+0.1N HCl) Inflexion 223 nm $E^1_1=319$; Inflexion 270 nm $E^1_1=329$; Max. 284 nm $E^1_1=284$.

EXAMPLE 11

Internal salt of 4-[[[7-[(2-amino-4-thiazolyl)(methoximino)-acetamido]-2-carboxy-8-oxo-4-thia-1-azabicyclo[4,2,0]oct-2-en-3-yl]-methyl]-thio]-1-methyl pyridinium (6S)(7S)(Z)

Step A: Iodide of 4-[[[2-[(2-tritylamino-4-thiazolyl)(2-methoxyimino)-acetamido]-8-oxo-2-(1,1-dimethyl)-ethyloxycarbonyl-4-thia-1-azabicyclo[4,2,0]oct-2-en-3-yl]-methyl]-thio]-1-methyl pyridinium (6S)(7S)(Z).

Under an inert atmosphere, 350 mg of (1,1-dimethyl)-ethyl (6S)(7S)(Z) -iodomethyl-7-[2-[2-(triphenylmethyl)-amino-4-thiazolyl]-2-methoxyimino]-acetamido]-8-oxo-4-thia-1-azabicyclo [4,2,0]oct-2-en-2-carboxylate, 3.5 ml of acetonitrile and 65 mg of 1-methyl-4-pyridine thione were mixed together and stirred at 20° C. for 2 hours, followed by concentrating to dryness by distilling under reduced pressure. The 440 mg of residue were chromatographed on silica and eluted with a mixture of methylene chloride and methanol (9/1) to obtain 320 mg of the product sought.

Step B: Internal salt of 4-[[[7-(2-amino-4-thiazolyl)-(methoxyimino)-acetamido]-2-carboxy-8-oxo-4-thia-1-azabicyclo [4,2,0]oct-2-en-3-yl]methyl-thio]-1-methyl pyridinium (6S)(7S)(Z)

(1) Detertbutylation and detritylation

Under an inert atmosphere, 280 mg of the product of Step A were mixed with 1.4 ml of trifluoroacetic acid with 10% of water and stirred at 20° C. for 50 minutes. 10 ml of ether were added slowly with stirring or 2 hours and then the precipitate formed was separated, washed and dried to obtain 184 mg of the deblocked product melting at 200° C.

(2) Obtaining the internal salt 180 mg of the said product were dissolved in 1.0 ml of acetonitrile and 1.0 ml of a 1M aqueous solution of triethylamine carbonate and the solution was fixed on a silica column (length 67 cm, diameter 2.7 cm) and was eluted successively with 1 liter of the following mixtures:

| Acetonitrile % | Water |
|---|---|
| 5 | 95 |
| 10 | 90 |
| 15 | 85 |
| 20 | 80 |

The fraction containing the expected product were collected and lyophilized to obtain 95 mg of the product sought melting at 200° C.

U.V. Spectrum. (ethanol) Max. 229 nm $E^1_1=452$, $\epsilon=23,500$; Inflexion 292 nm $E^1_1=409$; Max. 305 nm $E^1_1=463$, $\epsilon=24,100$.

U.V. Spectrum. (ethanol+0.1N HCl) Max. 229 nm $E^1_1=394$, $\epsilon=20,500$. Inflexion 276 nm $E^1_1=341$; Max. 300 nm $E^1_1=511$; $\epsilon=26,600$.

EXAMPLE 12

1:1 mixture of the iodide and trifluoroacetate of 2-[[7-[2-amino-4-thiazolyl)-(difluoromethoxyimino)-acetamido]-2-carboxy -8-oxo-4-thia]-1-azabicyclo[4,2,0]oct-2-en-3-yl]-methyl]-thio]-1-methyl pyridinium (6S)(7S)(Z) (trifluoracetate)

Step A: Exchange of iodine with 1-methylpyridine-2-thione

Under an inert atmosphere, 130 mg of 1,1-dimethylethyl (6S)(7S)(Z) 3-iodomethyl-7-[2-[2-triphenylmethyl-amino-4-thiazolyl]-[(difluoromethoxy)-imino]-acetamido]-8-oxo-4-thia -1-azabicyclo[4,2,0]oct-2-en-3-yl]-2-carboxylate, 1.5 ml of acetonitrile and 21 mg of 1-methyl-2-pyridine-thione were mixed together and stirred at 20° C. for 1 hour, followed by concentrating by dryness by distilling under reduced pressure. The residue was chromatographed on silica and eluted under nitrogen pressure with a mixture of methylene chloride and methanol (9/1) to obtain 102 mg of the product sought.

Step B: 1:1 mixture of the iodide and trifluoroacetate of 2-[[7-[(2-amino-4-thiazolyl)(difluoromethoxyimino)-acetamido]-2-carboxy-8-oxo-4-thia-1-azabicyclo[4,2,-0]oct-2-en-3-yl]-methyl]-thio]-1-methylpyridinium (6S)(7S)(Z)

Under an inert atmosphere, 102 mg of the product of Step A were mixed with 0.4 ml of trifluoroacetic acid with 10% of water and stirred at 20° C. for 1 hour. 6 ml of ether were added dropwise with stirring and the precipitate formed was separated, washed and dried to obtain 66 mg of the product sought with a Rf=0.5 on elution with a mixture of acetone and water (2/1)

U.V. Spectrum. (ethanol) Max. 221 nm $E^1_1=373$, $\epsilon=29,800$; Inflexion 246 nm $E^1_1=223$; Max. 307 nm $E^1_1=247$, $\epsilon=19,700$.

U.V. Spectrum. (ethanol+0.1N HCl) Inflexion 217 nm $E^1_1=327$, $\epsilon=26,100$; Max. 250 nm $E^1_1=239$, $\epsilon=19,100$; Inflexion 292 nm $E^1_1=226$, Max. 304 nm $E^1_1=239$, $\epsilon=19,100$.

EXAMPLE 13

Iodide of 2-[[[7-[(2-amino-4-thiazolyl)-(2-propenyloxyimino]-acetamido]-2-carboxy-8-oxo-4-thia-1-azabicyclo[4,2,-0]oct-2-en -3-yl]-methyl]-thio]-1-methyl pyridinium (trifluoroacetate) (6S)(7S)(Z)

(1) Exchange of iodine with 1-methylpyridine-2-thione.

Under an inert atmosphere, 117 mg of 1,1-dimethylethyl (6S)(7S)(Z) 3-iodomethyl-7-[3-[7-[(2-triphenylmethyl)-amino -4-thiazolyl[[(2-propenyloxyimino]-acetamido]-8-oxo-4-thia 1-azabicyclo[4,2,0]oct-2-en-3-yl]-2-carboxylate, 1.2 ml of acetonitrile and 18 mg of 1-methyl-pyridine-2-thione were mixed together and stirred at 20° C. for 90 minutes, followed by concentrating to dryness by distilling under reduced pressure. The residue was chromatographed on silica and eluted with a mixture of methylene chloride and methanol (90/10) to obtain 118 mg of the product sought which was used as is for the following reaction.

(2) Detritylation and detertbutylation 114 mg of the said product, 0.8 ml of trifluoroacetic acid and 0.05 ml of water were mixed together and stirred at 20° C. for 2 hour. 3.5 ml of ether were added slowly with stirring and the precipitate formed were separated, washed and dried under vacuum to obtain 58 mg of the product sought by a Rf=0.5 [elution with a mixture of acetone and water (2/1)].

U.V. Spectrum. (ethanol) Inflexion 213 nm $E^1_1=357$; Inflexion 222 nm $E^1_1=345$; Inflexion 231 nm $E^1_1=328$; Max. 305 nm $E^1_1=245$, $\epsilon=19,300$.

U.V. Spectrum. (ethanol+0.1N HCl) Inflexion 219 nm $E^1_1=340\times2$; Max. 252 nm $E^1_1=255\times2$, $\epsilon=20,100$; Max. 294 nm $E^1_1=243\times2$, $\epsilon=19,200$; Inflexion 307 nm $E^1_1=230\times2$.

EXAMPLE 14

Iodine and trifluoroacetate of (6S)(7S)(Z) 2-[[7-[(2-amino-4-thiazolyl)-[(fluoromethoxyimino)-acetamido]-2-carboxy-8-oxo-4-thia-1-azabicyclo[4,2,-0]oct-2-en-3-yl]-methyl]-thio]-1-methyl pyridinium (trifluoroacetate).

Step A: Exchange of hydroxyl with iodine

Under an inert atmosphere, 150 mg of 1,1-dimethylethyl (6S)(7S)(Z) 3-hydroxymethyl-7-[2-[2-triphenylmethylamino-4-thiazolyl]-[(difluoromethylimino]-acetamido]-8-oxo-4-thia-1-azabicyclo[4,2,-0]oct-2-en-3yl]-2-carboxylate, 3 ml of methylene chloride, 152 mg of Bu$_4$ $^+$I$^-$, and 96 µl of 2,6 lutidine were mixed together. Over about 10 minutes at −70° C., 1.4 ml of a solution of trifluoromethane sulfonic anhydride at 5% by volume in methylene chloride were added with stirring for 15 minute, followed by concentration to dryness by distilling under reduced pressure. The residue was chromatographed on silica and eluted with a mixture of methylene chloride and ethyl acetate (9/1) to obtain 120 mg of the iodized product sought which was used as for the following step.

Step B: Exchange of iodine with the 2-thio-1-methyl-pyridine base

Under an inert atmosphere, 100 mg of the product of derivative of Step A, 18 mg of 2-thio-1-methyl-pyridine and 4 ml of acetonitrile were mixed together and stirred at 20° C. for 1 hour, then concentrated to dryness by distilling under reduced pressure. The residue was chromatographed on silica and eluted with a mixture of methylene chloride and methanol (9/1) to obtain 100 mg of the product sought with a Rf=0.25 [elution with a mixture of methylene chloride and methanol (9/1)].

Step C: Iodide and trifluoroacetate of (6S)(7S)(Z) 2-7-(2-amino-4-thiazolyl)-[(fluoromethoxy)-imino]-acetamido]-2-carboxy -8-oxo-4-thia-1-azabicyclo[4,2,0]Oct-2-en-3-yl]-methyl]-thio]-1-methyl pyridinium (trifluoroacetate).

under an inert atmosphere, 100 mg of the product of Step B and 0.6 ml of trifluoroacetic acid at 10% in water were mixed together and stirred at 20° C. for one hour. The, 6 ml of ether were added with stirring for 10 minutes at 20° C. after which the precipitate formed was separated, washed and dried to obtain 65 mg of the product sought. Rf=0.7 on eluting with a mixture of 2 parts of acetone, 1 part water.

U.V. Spectrum. (ethanol) Max. 222 nm $E^1_1=403$, $\epsilon=31,500$; Inflexion 246 nm $E^1_1=236$; Max. 308 nm $E^1_1=250$, $\epsilon=19,500$.

U.V. Spectrum. (ethanol+0.1N HCl) Inflexion 218 nm $E^1_1=340$, $\epsilon=26,500$; Max. 253 nm $E^1_1=260$, $\epsilon=20,300$; Inflexion 300 nm $E^1_1=237$; Max. 312 nm $E^1_1=244$, $\epsilon=19,000$.

EXAMPLE 15

Internal salt of 2-[[3-[7-[(2-amino-4-thiazolyl)(methoxyimino)-acetamido-]-2-carboxy-8-4-thia-1-azabicyclo[4,2,0]oct-2-en-3-yl]-2(E)-propenyl]-thio]-1-methyl pyridinium (6S)(7S)(Z)

Step A: 1,1-dimethyl-ethyl (6S)(7S) 7-[2-(2-triphenylmethylaminothiazol-4-yl)-2-(Z) methoxyimino]-acetamido]-3-3(iodo propen-1-(E)-yl]-8-oxo-4-thia-1-azabicyclo[4,2,0]oct-2-en-2-carboxylate Under an inert atmosphere, 184 5 mg of 1,1-dimethylethyl (6S)(7S)-7-[2-(2-triphenylmethylaminthiazol-4-yl-2-(Z-methoxy imino]-acetamido]-3-(3-hydroxy-)propen-1-(E)-yl]-8-oxo-4-thia-1-azabicyclo[4,2,0]oct-2-en-2-carboxylate, 4 ml of methylene chloride, 120 mg of tetrabutylammonium iodide, and 116 µl of 2,6-lutidine were mixed together and the reaction mixture was taken to −70° C. At this temperature, there was introduced dropwise 620 µl of a solution of trifluoromethane sulfonic anhydride in methylene chloride titrating 0.609 mmoles/ml with stirring at −70° C. for 10 minutes. The temperature was allowed to return to 20° C. and the methylene chloride was eliminated by distilling under reduced pressure. A yellow solid was obtained which corresponded to the crude iodized derivative sought which was used immediately as is for the following step.

Step B: Iodide of
2-[[3-[7-[2-(2-triphenylmethylamino-4-thiazolyl)-(methoxyimino)-acetamido]-2-tertbutoxycarbonyl]-8-oxo-4-thia-1-azabicyclo[4,2,0]oct-2-en-3-yl]2-(E)-propenyl]-thio]-1-methyl pyridinium (6S)(7S)(Z)

Under an inert atmosphere, 320 mg of the iodized derivative of Step A, 7 ml of acetonitrile and 60 mg of 1-methylpyridin-2-thione-were mixed together and stirred at 20° C. for 90 minutes until a total dissociation was observed. The residue, after concentrating to dryness by distilling under reduced pressure, was chromatographed on silica and eluted with a mixture of methylene chloride and methanol (9/1) to obtain 251 mg of the product sought with a Rf=0.4 [elution with a mixture of methylene chloride and methanol (9/1)] and having a specific rotation of $[\alpha]_D = -120°$ (c=0.5% in chloroform).

U.V. Spectrum. (ethanol) Inflexion 238 nm $E^1_1=984$; Max. 315 nm $E^1_1=238$, $\epsilon=23,200$.

U.V. Spectrum. (ethanol+0.1N HCl) Inflexion 240 nm $E^1_1=307$; Max. 275 nm $E^1_1=251$, $\epsilon=24,400$; Max. 303 nm $E^1_1=244$, $\epsilon=23,700$; Inflexion 320 nm $E^1_1=233$, $\epsilon=22,700$.

Step C: 1:1 mixture of the iodide and trifluoroacetate of
2-[[3-[7-[(2-amino-4-thiazolyl)(methoxyimino)-acetamido]-2-carboxy-8-oxo-4-thia-1-azabicyclo-[4,2,0]oct-2-en-3-yl]-2-(E)-propenyl]thio]-1-methyl-pyridinium (6S)(7S)(Z)

Under an inert atmosphere, 218 mg of the product of Step B and 1.1 ml of trifluoroacetic acid with 10% of water were mixed together and stirred at 20° C. for 50 minutes. Then, 5 ml of ether were added slowly with stirring for 1 hour until the precipitate solidified and was then separated, washed and dried under vacuum to obtain 160 mg of the product sought with an Rf=0.35 [elution with a mixture of acetone and water (2/1)].

Step D: Internal salt of
2-[[3-[7-[2-amino-4-thiazolyl)-(methoxyimino)-acetamido]-2-carboxy-8-oxo-4-thia-1-azabicyclo[4,2,0]oct-2-en-3-yl-2-(E)-propenyl]-thio]-1-methyl pyridinium (6S)(7S)(Z)

Under an inert atmosphere, 160 mg of the product of Step C, 1,5 ml of acetonitrile and 1 ml of triethylamine carbonate were mixed together and purified by H.P.L.C. on a column 67 cm in length and 27 mm in diameter (filled with RP 18). Elution was done with the following mixtures:

| Acetonitrile % | Water |
| --- | --- |
| 5 | 95 |
| 10 | 90 |
| 15 | 85 |
| 20 | 80 |

The fractions containing the expected product were combined and concentrated to dryness to obtain 45.5 mg of the expected product melting at about 200° C. (with decomposition) and having a Rf=0.35 [elution with a mixture of acetone and water (2/1)].

U.V. Spectrum. (ethanol+0.1N HCl) Inflexion 240 nm $E^1_1=337$, $\epsilon=18,400$; Max. 280 nm $E^1_1=451$, $\epsilon=24,650$; Inflexion 320 nm $E^1_1=242$, $\epsilon=13,600$.

EXAMPLE 16

Mixture of iodide and trifluoroacetate of (6S)(7S)(Z)
2-[[[7-[(2-amino-4-thiazolyl)-(methoxyimino)-acetamido]-2-carboxy-8-oxo-4-thia-1-azabicyclo[4,2,0]oct-2-en-3-yl]-methyl]-thio]-1-(carboxymethyl)-pyridinium (6S)(7S)(Z)

Using the procedure of Example 1, 85 mg of 1-tert-butyloxy acetyl-pyridin-2-thione and 300 mg of 1,1-dimethylethyl 7-[(2-tritylamino-4-thiazol) (methoxyiminoz)-acetamido]-8-oxo-4-thia-1-azabicyclo[4,2,0]-oct-2-en-3-yl]-3-iodomethyl-2-carboxy late were reacted to obtain 222 mg of the iodide of the still protected product. 204 mg of this latter were treated as in Example 2 to obtain 45 mg of the expected product.

U.V. Spectrum. (ethanol) Max. 221 nm $E^1_1=380$, $\epsilon=30,700$; Max. 305 nm $E^1_1=225$, $\epsilon=18,100$.

U.V. Spectrum. (ethanol=0.1N HCl) Max. 220 nm $E^1_1=345$, $\epsilon=27,800$; Max. 256 nm $E^1_1=263$, $\epsilon=21,200$; Inflexion 284 nm $E^1_1=230$; Inflexion 283 nm $E^1_1=229$, $\epsilon=18,500$; Inflexion 308 nm $E^1_1=210$.

EXAMPLE 17

Internal salt of
2-[[[7-[2-(2-amino-4-thiazolyl)(methoxyimino)-acetamido]-2-carboxy-8-oxo-4-thia-1-azabicyclo[4,2,0]oct-2-en-3-yl]-methyl]-thio]-1-propyl-pyridinium (6S)(7S)(Z)

Using the procedure of Example 16, 78 mg of 1-propylpyridin-2-thione were reacted to obtain 170 mg of product which was purified by H.P.L.C. chromatography by dissolving it in 0.9 ml of acetonitrile and 0.9 ml of an (M) solution of triethylamine carbonate, and by eluting successively with aqueous solutions with 5, 10, 15 and 20% of acetonitrile. The fractions of interest were lyophilized to obtain 71 mg of the expected product.

U.V. Spectrum. (ethanol) Inflexion 230 nm $E^1_1=388$; Inflexion 249 nm $E^1_1=295$; Max. 295 nm $E^1_1=300$, $\epsilon=16,500$; Inflexion 310 nm $E^1_1=265$.

U.V. Spectrum. (ethanol+0.1N HCl) Inflexion 222 nm $E^1_1=328$; Inflexion 266 nm $E^1_1=304$; Inflexion 273 nm $E^1_1=306$; Max. 284 nm $E^1_1=322$, $\epsilon=17,700$; Inflexion 290 nm $E^1_1=318$; Inflexion 309 nm $E^1_1=278$.

EXAMPLE 18

Internal salt of
2-[[[7-[2-(2-amino-4-thiazolyl)-(methoxyimino)-acetamido]-2-carboxy-8-oxo-4-thia-1-azabicyclo[4,2,0]oct-2-en-3-yl]-methyl]-thio]-1-(2-propenyl) pyridinium (6S)(7S)(Z)

Using the procedure of Example 17, 85 mg of 1-(2-propenyl) -2-pyridin-thione were reacted to obtain 60 mg of lyophlized product.

U.V. Spectrum. (ethanol) Inflexion 230 nm $E^1_1=399$; Max. 291 nm $E^1_1=313$, $\epsilon=17,100$; Inflexion 370 nm $E^1_1=35$.

U.V. Spectrum. (ethanol+0.1N HCl) Inflexion 230 nm $E^1_1=309$; Inflexion 270 nm $E^1_1=323$; Max. 284 nm $E^1_1=345$, $\epsilon=19,000$; Inflexion 310 nm $E^1_1=264$.

EXAMPLE 19

Trifluoroacetate of 6-[[[7-[(2-amino-4-thiazolyl)-(methoxyimino)-acetamido]-2-carboxy-8-oxo-4-thia-1-azabicyclo[4,2,0]oct-2-en-3-yl]-methyl]-thio]-7-methyl (thieno)[2,3-b]pyridinium (6S)(7S)(Z) trifluoroacetate Using the procedure of Example 16, 7-methyl-thieno[2,3-b]pyridin-6-thione was reacted to obtain 93 mg of the expected product.

U.V. Spectrum. (ethanol) Max. 239 nm $E^1{}_1=368$, $\epsilon=29,600$; Max. 300 nm $E^1{}_1=201$, $\epsilon=16,200$; Max. 342 nm $E^1{}_1=141$, $\epsilon=11,400$.

U.V. Spectrum. (ethanol+0.1N HCl) Max. 247 nm $E^1{}_1=339$, $\epsilon=27,300$; Max. 286 nm $E^1{}_1=217$, $\epsilon=17,500$; Max. 343 nm $E^1{}_1=150$, $\epsilon=12,100$.

EXAMPLE 20

Internal salt of 2-[[[7-[2-(2-amino-4-thiazolyl)(methoxyimino)-acetamido]-2-carboxy-8-oxo-4-thia-1-azabicyclo[4,2,0]oct-2-en-3-yl]-methyl]-thio]-6-methylthio-1-methyl pyridinium (6S)(7S)(Z)

Using the procedure of Example 17, 109 mg of 6-methylthio-1-methyl-pyridin-2-thione were reacted to obtain 85 mg of the expected product.

U.V. Spectrum. (ethanol) Max. 225 nm $E^1{}_1=462$, $\epsilon=26,200$; Inflexion 260 nm $E^1{}_1=254$; Max. 291 nm $E^1{}_1=273$, $\epsilon=15,500$; Max. 350 nm $E^1{}_1=214$; $\epsilon=12,100$; Inflexion 380 nm $E^1{}_1=59$.

U.V. Spectrum. (ethanol+0.1N HCl) Max. 225 nm $E^1{}_1=370$, $\epsilon=21,000$; Max. 261 nm $E^1{}_1=327$, $\epsilon=18,500$; Max. 283 nm $E^1{}_1=304$, $\epsilon=17,200$; Max. 350 nm $E^1{}_1=223$, $\epsilon=12,600$.

EXAMPLE 21

Internal salt of 2-[[[7-[2-(2-amino-4-thiazolyl)(methoxyimino)-acetamido]-2-carboxy-8-oxo-4-thia-1-azabicyclo[4,2,0]oct-2-en-3-yl]-methyl]-thio]-1-(methylthio)-methyl pyridinium (6S)(7S)(Z)

Using the procedure of Example 17, 73 mg of 1-methylthiomethyl-2-pyridin-thione were reacted to obtain 65 mg of the expected product melting at 200° C.

U.V. Spectrum. (ethanol) Inflexion 230 nm $E^1{}_1=395$, $\epsilon=22,400$; Inflexion 250 nm $E^1{}_1=260$; Max. 291 nm $E^1{}_1=311$, $\epsilon=17,600$; Inflexion 330 nm $E^1{}_1=140$; Inflexion 370 nm $E^1{}_1=44$.

U.V. Spectrum. (ethanol+0.1N HCl) Inflexion 266 nm $E^1{}_1=318$; Inflexion 275 nm $E^1{}_1=333$; Max. 285 nm $E^1{}_1=350$, $\epsilon=19,800$; Inflexion 315 nm $E^1{}_1=225$; Inflexion 370 nm $E^1{}_1=45$.

EXAMPLE 22

Internal salt of 4-[[[7-[2-(2-amino-4-thiazolyl)-(methoxyimino)-acetamido]-2-carboxy-8-oxo-4-thia-1-azabicyclo[4,2,0]oct-2-en-3-yl]-methyl-thio]-1-(1-methyl)-ethyl pyridinium (6S)(7S)(Z)

Using the procedure of Example 17, 76 mg of 1-(1-methyl)-ethyl-4-pyridine thione were reacted to obtain 95 mg of the expected product.

U.V. Spectrum. (methanol) Inflexion 222 nm $E^1{}_1=434$; Max. 230 nm $E^1{}_1=461$, $\epsilon=25,300$; Inflexion 296 nm $E^1{}_1=441$; Max. 306 nm $E^1{}_1=477$, $\epsilon=26,200$; Inflexion 340 nm $E^1{}_1=79$.

U.V. Spectrum. (ethanol+0.1N HCl) Max. 230 nm $E^1{}_1=460$, $\epsilon=25,200$; Inflexion 270 nm $E^1{}_1=309$; Max. 303 nm $E^1{}_1=518$, $\epsilon=28,400$.

EXAMPLE 23

Iodide of 4-[[[7-[2-(2-amino-4-thiazolyl)(methoxyimino)acetamido]-2-carboxy-8-oxo-4-thia-1-azabicyclo[4,2,0]oct-2-en-3-yl]-methyl]-thio]-6,7-dihydro-1-methyl)-5H-1-pyridinium (6S)(7S)(Z)

Using the procedure of Example 6, 80 mg of 1-methyl-cyclopentano-(b)-4-thiopyridone were reacted without potassium carbonate. After chromatographing on silica, eluting with a mixture of methylene chloride and methanol (95/5) then (90/10), 370 mg of the iodide of the blocked product were obtained. 315 mg of this latter were treated with 3.15 ml of formic acid with 33% of water for 8 hours at 50° C. After filtering, the filtrate was concentrated to dryness under reduced pressure, and the residue was stirred for 1 hour in 3.15 ml of ethyl acetate. By separating, 206 mg of the expected product were obtained with a specific rotation of $[\alpha]_D = -44° \pm 1.5$ (c=0.6% in DMSO)

U.V. Spectrum. (ethanol) Inflexion 216 nm $E^1{}_1=497$, $\epsilon=34,200$; Inflexion 231 nm $E^1{}_1=422$; Max. 292 nm $E^1{}_1=407$, $\epsilon=28,000$; Inflexion 330 nm $E^1{}_1=91$.

U.V. Spectrum. (ethanol+0.1N HCl) Max. 219 nm $E^1{}_1=443$, $\epsilon=30,500$; Max. 299 nm $E^1{}_1=427$, $\epsilon=29,400$.

EXAMPLE 24

Mixture of iodide and trifluoroacetate of 2-[[[7-[2-(2-amino-4-thiazolyl)(methoxyimino)-acetamido]-2-carboxy-8-oxo-4-thia-1-azabicyclo[4,2,0]oct-2-en-3-yl]-methyl-thio]-1-[(methoxycarbonylmethyl) pyridinium (trifluoroacetate) (6S)(7S)(Z)

Using the procedure of Example 16, 80 mg of 1-[(methoxycarbonyl)-methyl]-pyridin-2-thione were reacted to obtain 85 mg of the expected product.

U.V. Spectrum. (ethanol) Max. 218 nm $E^1{}_1=342$, $\epsilon=28,100$; Max. 294 nm $E^1{}_1=196$, $\epsilon=16,100$; Inflexion 350 nm $E^1{}_1=70$.

U.V. Spectrum. (ethanol+0.1N HCl) Max. 218 nm $E^1{}_1=308$, $\epsilon=25,300$; Max. 260 nm $E^1{}_1=232$, $\epsilon=19,000$; Max. 284 nm $E^1{}_1=223$, $\epsilon=18,300$; Inflexion 360 nm $E^1{}_1=43$.

EXAMPLE 25

Iodide of 4-[[[7-[2-amino-4-thiazolyl)(methoxyimino)-acetamido]-2-carboxy-8-oxo-4-thia-1-azabicyclo[4,2,0]oct-2-en-3-yl]-methy]-thio]-1-(2-fluoroethyl)-pyridinium (6S)(7S)(Z)

Using the procedure of Example 23, 1-(2-fluoroethyl)pyridin-4-thione were reacted to obtain 128 mg of the expected product melting at 210° C. and having a specific rotation of $[\alpha]_D = -39.5° \pm 1.5$ (c=0.6% in DMSO).

U.V. Spectrum. (ethanol) Max. 221 nm $E^1{}_1=493$, $\epsilon=33,500$; Inflexion 230 nm $E^1{}_1=450$; Max. 308 nm $E^1{}_1=399$, $\epsilon=27,200$.

U.V. Spectrum. (ethanol+0.1N HCl) Max. 222 nm $E^1{}_1=456$, $\epsilon=31,000$; Inflexion 270 nm $E^1{}_1=248$; Max. 260 nm $E^1{}_1=421$, $\epsilon=28,600$.

EXAMPLE 26

Mixture of iodide and trifluoroacetate of
4-[[[7-[2-amino-4-thiazolyl)(methoxyimino)-acetamido]-2-carboxy-8-oxo-4-thia-1-azabicyclo[4,2,0]oct-2-en-3-yl]-methyl]-thio]-1-(carboxymethyl)pyridinium trifluoroacetate (6S)(7S)(Z)

Using the procedure of Example 24, 113 mg of 1-[(methoxycarbonyl)-methyl]-pyridin-4-thione were reacted to obtain 130 mg of the expected product.

U.V. Spectrum. (ethanol) Max. 227 nm $E^1_1=379$, $\epsilon=30,600$; Max. 309 nm $E^1_1=406$, $\epsilon=32,700$.

U.V. Spectrum. (ethanol+0.1N HCl) Max. 227 nm $E^1_1=326$, $\epsilon=25,300$; Max. 264 nm $E^1_1=234$, $\epsilon=18,900$; Max. 308 nm $E^1_1=393$, $\epsilon=31,700$.

EXAMPLE 27

4-[[[7-[2-amino-4-thiazolyl)(methoxyimino)-acetamido]-2-carboxy-8-oxo-4-thia-1-azabicyclo[4,2,0]oct-2-en-3-yl]-methyl]-thio]-1-[(aminothiocarbonyl)-methyl]-pyridinium (6S)(7S)(Z)

Using the procedure of Example 23, 45 mg of 1-[(aminothiocarbonyl)-methyl]-pyridin-4-thione were reacted to obtain 116 mg of the expected product having a specific rotation of $[\alpha]_D = -60°\pm 1.5°$ (c=0.6% in DMSO).

U.V. Spectrum. (ethanol) Max. 221 nm $E^1_1=500$, $\epsilon=35,400$; Max. 265 nm $E^1_1=263$, $\epsilon=24,300$; Inflexion 301 nm $E^1_1=343$; Max. 309 nm $E^1_1=366$, $\epsilon=25,900$.

U.V. Spectrum. (ethanol+0.1N HCl) Max. 223 nm $E^1_1=462$, $\epsilon=32,700$; Max. 269 nm $E^1_1=348$, $\epsilon=24,600$; Inflexion 302 nm $E^1_1=380$; Max. 309 nm $E^1_1=386$, $\epsilon=27,300$.

EXAMPLE 28

Iodide of
4-[[[7-[(2-amino-4-thiazolyl)(1-carboxy-1-methylethoxy)-imino-acetamido]-2-carboxy-8-oxo-4-thia-1-azabicyclo [4,2,0]oct-2-en-3-yl-]methyl]-thio-]-1-methyl]-pyridinium (6S)(7S)(Z) (trifluoroacetate).

Using the procedure of Example 2, 150 mg of 1,1-dimethylethyl 7-[(2-amino-4-thiazolyl)(1-carboxy-1-methylethoxyimino)acetamido]-8-oxo-4-thia-1-azabicyclo[4,2,0]oct-2-en-3-yl]-3-iodomethyl 2-carboxylate were reacted to obtain 78 mg of the expected product.

U.V. Spectrum. (ethanol) Max. 227 nm $E^1_1=362$, $\epsilon=30,600$; Max. 305 nm $E^1_1=340$, $\epsilon=28,800$.

U.V. Spectrum. (ethanol+0.1N HCl) Max. 225 nm $E^1_1=306$, $\epsilon=25,900$; Inflexion 267 nm $E^1_1=229$; Max. 300 nm $E^1_1=357$, $\epsilon=30,200$.

EXAMPLE 29

Iodide of
2-[[[7-[(2-amino-4-thiazolyl)[(1-carboxy-1-methylethoxy)-imino-acetamido]-2-carboxy-8-oxo-4-thia-1-azabicyclo [4,2,0]oct-2-en-3-yl]-methyl-thio]-1-methyl pyridinium (6S)(7S)(Z) (trifluoroacetate).

Using the procedure of Example 28, 1-methyl-pyridin-2-thione were reacted to obtain 89 mg of the expected product.

U.V. Spectrum. (ethanol+0.1N HCl) Inflexion 218 nm $E^1_1=265$, $\epsilon=22,400$; Max. 255 nm $E^1_1=221$, $\epsilon=18,700$; Inflexion 267 nm $E^1_1=209$.

Inflexion 286 nm $E^1_1=207$; Max. 294 nm $E^1_1=209$, $\epsilon=17,700$; Inflexion 307 nm $E^1_1=202$.

EXAMPLE 30

Trifluoroacetate of
2-[[[7-[(2-amino-4-thiazolyl)-(methoxyimino)-acetamido]-2-carboxy-8-oxo-4-thia-1-azabicyclo[4,2,0]oct-2-en-3-yl]-methyl-thio]-quinolizinium (6S)(7S)(Z) (trifluoroacetate)

Using the procedure of Example 16, quinolizin-4-thione were reacted to obtain 112.6 mg of the expected product.

U.V. Spectrum. (ethanol) Max. 216 nm $E^1_1=576$, $\epsilon=45,000$; Inflexion 227 nm $E^1_1=486$; Inflexion 240 nm $E^1_1=400$; Inflexion 262 nm $E^1_1=311$; Max. 298 nm $E^1_1=275$, $\epsilon=21,600$; Max. 348 nm $E^1_1=290$, $\epsilon=22,800$.

U.V. Spectrum. (ethanol+0.1N HCl) Max. 215 nm $E^1_1=520$, $\epsilon=40,800$; Inflexion 228 nm $E^1_1=420$; Inflexion 252 nm $E^1_1=384$; Max. 263 nm $E^1_1=399$, $\epsilon=31,300$; Max. 297 nm $E^1_1=294$, $\epsilon=23,100$; Max. 348 nm $E^1_1=321$, $\epsilon=25,200$; Inflexion 288, 308 nm.

EXAMPLE 31

Iodide of
4-[[[7-[(2-amino-4-thiazolyl)-(cyclopropyl-methoxyimino)-acetamido]-2-carboxy-8-oxo-4-thia-1-azabicyclo[4,2,0]oct -2-en-3-yl]-methyl-thio]-1-methyl pyridinium (trifluoroacetate) (6S)(7S)(Z)

Using the procedure of Example 16, 200 mg of 1,1-dimethylethyl 7-[(2-tritylamino-4-thiazolyl)-(cyclopropyl-methoxyimino)acetamido]-2-carboxy-8-oxo-4-thia-1-azabicyclo[4,2,0]oct-2-en-3-yl]-3-iodomethyl]-2-carboxylate and 40 mg of 1-methyl-4-thiopyridinone were reacted to obtain 47 mg of the expected product.

U.V. Spectrum. (ethanol) Max. 227 nm $E^1_1=404$, $\epsilon=32,400$; Max. 305 nm $E^1_1=394$, $\epsilon=31,600$.

U.V. Spectrum. (ethanol+0.1N HCl) Max. 226 nm $E^1_1=364$, $\epsilon=29,200$; Inflexion 260 nm $E^1_1=234$; Inflexion 274 nm $E^1_1=272$; Max. 300 nm $E^1_1=424$; $\epsilon=34,000$.

EXAMPLE 32

Iodide of
4-[[[7-[(2-amino-4-thiazolyl)-(2-bromo-2-propenyloxyimino)-acetamido]-2-carboxy-8-oxo-4-thia-1-azabicyclo[4,2,0]oct-2-en-3-yl]-methyl]-thio]-1-methyl pyridinium (trifluoroacetate) (6S)(7S)(Z).

Using the procedure of Example 31, 180 mg of 1,1-dimethylethyl 7-[(2-tritylamino-4-thiazolyl)-(2-bromo-2-propenyloxyimino)-acetamido]-8-oxo-4-thia-1-azabicyclo[4,2,0]oct-2-en-3-yl]-3-iodomethyl]-2-carboxylate were reacted to obtain 75 mg of the expected product.

U.V. Spectrum. (ethanol) Max. 227 nm $E^1_1=354$, $\epsilon=30,700$; Max. 305 nm $E^1_1=322$, $\epsilon=27,900$.

U.V. Spectrum. (ethanol+0.1N HCl) Max. 223 nm $E^1_1=318$, $\epsilon=27,600$; Inflexion 262 nm $E^1_1=223$; Max. 300 nm $E^1_1=335$, $\epsilon=29,100$.

EXAMPLE 33

1:1 mixture of the iodide and trifluoroacetate of
2-[[[7-[(2-amino-4-thiazolyl)-(fluoroethoxyimino)-acetamido]-2-carboxy-8-oxo-4-thia-1-azabicyclo[4,2,0]oct-2-en-3-yl]-methyl]-thio]-1-methyl pyridinium (trifluoroacetate) (6S)(7S)(syn)

Using the procedure of Example 12, 1,1-dimethylethyl 7-[(2-tritylamino-4-thiazolyl)-(fluoroethyoxyimino)-acetamido]-2-carboxy-8-oxo-4-thia-1-azabicyclo[4,2,0]oct-2-en-3-yl]-3-iodomethyl-2-carboxylate was reacted to obtain 81 mg of the expected product.

U.V. Spectrum. (ethanol) Max. 220 nm $E^1_1=334$, $\epsilon=31,400$; Max. 309 nm $E^1_1=226$, $\epsilon=21,200$.

U.V. Spectrum. (ethanol+0.1N HCl) Inflexion 218 nm $E^1_1=302$; Inflexion 250 nm $E^1_1=228$; Max. 305 nm $E^1_1=217$, $\epsilon=20,400$.

EXAMPLE 34

Internal salt of 4-[[[7-[(5-amino-1,2,4-thiadiazol-3-yl) (methoxyimino)-acetamido]-2-carboxy-8-oxo-4-thia-1-azabicyclo [4,2,0]oct-2-en-3-yl]-methyl]-thio]-1-methyl pyridinium (6R,S) (7R,S)(Z)

426 mg of 1,1-dimethylethyl 7-[(5-tritylamino-1,2,4-thiadiazol-3-yl)-(methoxyimino)-acetamido]-3-iodomethyl-8-oxo-4-thia-1-azabicyclo[4,2,0]oct-2-en-3-yl]-2-carboxylate (6S)(7S)(Z) in 4 ml of dry acetonitrile and 65 mg of 1-methyl-4-pyridin-thione were stirred for half an hour at ambient temperature and evaporated to dryness at 30° C. under reduced pressure. The residue was chromatographed on silica and eluted with a mixture of methylene chloride-methanol (95/5) to obtain 428 mg of blocked product. 395 mg of the latter were stirred with 7.2 ml of trifluoroacetic acid with 10% of anisole for 10 minutes and then filtered. The filtrate was added dropwise into 7.5 ml of isopropyl ether under vigorous stirring and by centrifuging, 258.5 mg of crude product were obtained. After H.P.L.C. chromatography on lichrosorb with elution by a mixture of water and acetonitrile (85/15), then lyophiliation, 130 mg of the expected product were obtained.

U.V. Spectrum. (ethanol) Max. 230 nm $E^1_1=485$, $\epsilon=25,300$; Inflexion 295 nm $E^1_1=411$; Max. 305 nm $E^1_1=441$, $\epsilon=23,000$; Inflexion 340 nm $E^1_1=63$.

U.V. Spectrum. (ethanol+0.1N HCl) Max. 230 nm $E^1_1=522$, $\epsilon=27,200$; Max. 305 nm $E^1_1=491$, $\epsilon=25,600$.

EXAMPLE 35

Internal salt of 2-[[[7-[(5-amino-1,2,4-thiadiazol-3-yl) (methoxyimino)-acetamido]-2-carboxy-8-oxo-4-thia-1-azabicyclo [4,2,0]oct-2-en-3-yl]-methyl]-thio]-1-methyl pyridinium (6R,S)(7R,S)(Z)

117.8 mg of 1,1-dimethylethyl 7-[(5-amino-1,2,4-thiadiazol-3-yl)-(methoxyimino)-acetamido]-2-carboxy-8-oxo-4-thia-1-azabicyclo[4,2,0]oct-2-en-3-yl]-3-chloromethyl-2-carboxylate, 54.2 mg of sodium iodide, 30.2 mg of 1-methyl-2-pyridin-thione and 1.7 ml of dry acetonitrile were stirred for 1 hour at 50° C. After concentrating to dryness, the residue was chromatographed on silica and eluted with a mixture of methylene chloride-methanol (75/25) to obtain 127 mg of iodide of 1,1-dimethylethyl 2-[[[7-[(5-amino-1,2,4-thiadiazol-3-yl)(methoxyimino)-acetamido]-2-oxo-4-thia-1-azabicyclo[4,2,0]oct-2-en-3-yl]methyl]-thio]-1-methyl pyridinium-2-carboxylate. 126 mg of the latter were stirred for a quarter of an hour with 3 ml of trifluoroacetic acid with 10% of anisole and the insoluble matter was filtered off. The filtrate was added dropwise to 30 ml of isopropyl ether under vigorous stirring. 104 mg of crude product were obtained by centrifuging. H.P.L.C. chromatography was carried out on lichrosorb and elution with a mixture of water and acetonitrile (85/15) yielded, after lyophilizing, 19 mg of the expected product.

U.V. Spectrum. (ethanol) Max. 230 nm $E^1_1=464$, $\epsilon=24,200$; Max. 292 nm $E^1_1=279$, $\epsilon=14,600$; Inflexion 308 nm $E^1_1=250$.

U.V. Spectrum. (ethanol+0.1N HCl) Max. 231 nm $E^1_1=476$, $\epsilon=24,800$; Inflexion 296 nm $E^1_1=266$; Max. 310 nm $E^1_1=292$, $\epsilon=15,200$.

EXAMPLE 36

Internal salt of 4-[[[7-[(2-(2-amino-4-thiazolyl)-2-(methoxyimino)-acetamido]-2-carboxy-8-oxo-4-thia-1-azabicyclo[4,2,0]oct-2-en-3-yl]-methyl]-thio]-1-ethyl-3-methyl pyridinium (6S)(7S)(Z)

Using the procedure of Example 17, 80 mg of 1-ethyl-3-methyl-4-pyridine thione were reacted to obtain 66 mg of the expected product.

U.V. Spectrum. (ethanol+0.1 N HCl)
Max. 230 nm $E^1_1=425$, $\epsilon=23,400$;
Inflexion 276 nm $E^1_1=368$;
Max. 300 nm $E^1_1=575$, $\epsilon=31,600$.

EXAMPLE 37

Trifluoroacetate of 2-[[[7-[(2-amino-4-thiazolyl)-(methoxyimino)acetamido]-2-carboxy-8-oxo-4-thia-1-azabicyclo[4,2,0]oct-2-en-3-yl]-methyl]-thio]-1-methyl-3,4,5,6-tetrahydro-pyridinium (trifluoroacetate) (6S) (7S) (Z)

Using the procedure of Example 5 up to 1 of Step C, 26 mg of N-methylpyridine-2-thione were reacted to obtain 104 mg of the expected product.

U.V. Spectrum. (ethanol)
Max. 220 nm $E^1_1=393$, $\epsilon=29,600$;
Max. 301 nm $E^1_1=180$, $\epsilon=13,600$.
U.V. Spectrum. (ethanol+0.1 N HCl)
Max. 220 nm $E^1_1=349$, $\epsilon=26,300$;
Inflexion 255 nm $E^1_1=183$;
Max. 291 nm $E^1_1=201$, $\epsilon=15,100$.

EXAMPLE 38

Iodide of 4-[[[7-[[2-(2-amino-4-thiazolyl)-2-(methoxyimino)acetamido]-2-carboxy-8-oxo-4-thia-1-azabicyclo[4,2,0]oct-2-en-3-yl)-methyl]-thio]-1,3-dimethyl-pyridinium (6S) (7S) (Z)

Using the procedure of Example 23, 39 mg of 1,3-dimethyl-4-thio-pyridinone were reacted to obtain 116 mg of the expected product with a specific rotation of $[\alpha]_D = -22° \pm 1.5°$ (c=0.5% in DMSO).
U.V. Spectrum. (ethanol)
Max. 220 nm $E^1_1=530$, $\epsilon=35,100$;
Max. 302 nm $E^1_1=423$, $\epsilon=28,000$.
U.V. Spectrum. (ethanol+0.1 N HCl)
Max. 221 nm $E^1_1=489$, $\epsilon=32,400$;
Inflexion 264 nm $E^1_1=260$;
Inflexion 270 nm $E^1_1=282$;
Max. 299 nm $E^1_1=454$, $\epsilon=20,100$.

Using the procedure of the preceding examples, the following examples have been prepared:

EXAMPLE 39

Internal salt of 2-[[[7-[2-(2-amino-4-thiazolyl)-2-(methoxyimino)-acetamido]-2-carboxy-8-oxo-4-thia-1-azabicyclo[4,2,-0]oct-2-en-3-yl]-methyl]-thio]-quinolizinium (6S) (7S) syn.

| NMR Spectrum (DMSO) 250 MHz. | |
|---|---|
| 6.77 ppm | H5 of the thiazol |
| 3.82 ppm | H of the methoxyimino |

-continued

| NMR Spectrum (DMSO) 250 MHz. | | |
|---|---|---|
| 5.44 ppm | $H_7$ | } isocephene |
| 3.90 ppm | $H_6$ | |
| 4.55–4.73 ppm | H of the $CH_2$ in position 3-alpha of S | |
| 8.83 ppm | $H_1$ of the quinoziline | |
| 7.85 to 8.23 ppm | other aromatic protons. | |

EXAMPLE 40

(6S) (7S) (Z) Iodide of 2-[[[7-[2-(2-amino-4-thiazolyl)-[[2-[(difluoromethyl)-thio]-ethoxy]-imino]-acetamido]-2-carboxy-8-oxo-4-thia-1-azabicyclo[4,2,0]oct-2-en-3-yl]-methyl]-thio]-1-methyl pyridinium (trifluoroacetate)

U.V. Spectrum. (EtOH)
Inflexion 217 nm
Max. 302 nm $E^1_1=221$, $\epsilon=19,000$;
Inflexion 360 nm.
U.V. Spectrum. (EtOH+0.1 N HCl)
Inflexion 217 nm
Max. 255 nm $E^1_1=225$, $\epsilon=19,300$;
Max. 294 nm $E^1_1=218$, $\epsilon=18,700$;
Inflexion 310 nm.

EXAMPLE 41

(6S) (7S) (Z) Iodide of 4-[[[7-[2-(2-amino-4-thiazolyl)-[(difluoromethoxy)-imino]-acetamido]-2-carboxy-8-oxo-4-thia-1-azabicyclo[4,2,0]oct-2-en-3-yl]-methyl]-thio]-1,3-dimethyl pyridinium (trifluoroacetate)

U.V. Spectrum. (EtOH)
Max. 223 nm $E^1_1=392$, $\epsilon=31,900$;
Max. 305 nm $E^1_1=365$, $\epsilon=29,700$.
U.V. Spectrum. (EtOH+0.1 N HCl)
Max. 226 nm $E^1_1=317$, $\epsilon=25,800$;
Max. 257 nm $E^1_1=209$, $\epsilon=17,000$;
Max. 300 nm $E^1_1=384$, $\epsilon=31,200$.

EXAMPLE 42

Iodide of 3-[[[7-[2-(2-amino-4-thiazolyl)-2-(methoxyimino]acetamido]-2-carboxy-8-oxo-4-thia-1-azabicyclo[4,2,0]oct-2-en-3-yl]-methyl]-thio]-1-methyl pyridinium (6S) (7S) (Z) (trifluoroacetate)

Melting at about 220° C. and having a specific rotation of $[\alpha]_D=-17°\pm2°$ (c=0.6% in DMSO).

EXAMPLE 43

(6S) (7S) (Z) Iodide of 4-[[[7-[2-amino-4-thiazolyl)[(fluoro methoxyimino]-acetamido]-2-carboxy-8-oxo-4-thia-1-azabicyclo[4,2,0]oct-2-en-3-yl]-methyl]-thio]-1,3-dimethyl pyridinium (trifluoroacetate)

U.V. Spectrum. (EtOH)
Max. 226 nm $E^1_1=385$, $\epsilon=30,600$;
Max. 303 nm $E^1_1=357$, $\epsilon=28,400$.
U.V. Spectrum. (EtOH+0.1 N HCl)
Max. 226 nm $E^1_1=312$, $\epsilon=24,800$;
Inflexion 263 nm;
Max. 299 nm $E^1_1=372$, $\epsilon=29,600$;
Max. 300 nm $E^1_1=384$, $\epsilon=31,200$.

EXAMPLE 44

(6S) (7S) (Z) 2-[[[7-[2-(2-amino-4-thiazolyl)-2-(methoxyimino]acetamido]-2-carboxy-8-oxo-4-thia-1-azabicyclo[4,2,0]oct-2-en-3-yl]-methyl]-thio]-5-aminocarbonyl-1-methyl pyridinium melting at about 190° C. and having a specific rotation of $[\alpha]_D=-17°\pm1°$ (c=0.6% in DMSO)

EXAMPLE 45

Iodide of 4-[[[7-[(2-amino-4-thiazolyl)-2-(methoxyimino]acetamido]-2-carboxy-8-oxo-4-thia-1-azabicyclo[4,2,0]oct-2-en-3-yl]-methyl]-thio]-3-methyl-1-[methoxycarbonyl)-methyl]pyridinium (6S) (7S) (Z)

Melting at about 220° C. and having a specific rotation of $[\alpha]_D=-19.5°\pm1°$ (c=0.6% in DSMO)

EXAMPLE 46

Internal salt of 4-[[[7-[2-(2-amino-4-thiazolyl)-(methoxyimino]acetamido]-2-carboxy-8-oxo-4-thia-1-azabicyclo[4,2,0]oct-2-en-3-yl]-methyl]-thio]-1-methyl-5,6-dihydro pyridinium (6S) (7S) (Z)

U.V. Spectrum. (EtOH)
Inflexion 223 nm
Max. 228 nm $E^1_1=427$, $\epsilon=32,300$;
Max. 303 nm $E^1_1=420$, $\epsilon=21,900$;
Inflexion 356 nm.
U.V. Spectrum. (EtOH+0.1 N HCl)
Max. 227 nm $E^1_1=357$, $\epsilon=18,700$;
Inflexion 266 nm;
Inflexion 274 nm;
Max. 298 nm $E^1_1=457$, $\epsilon=23,900$.

EXAMPLE 47

Internal salt of (6S) (7S) (Z) 4-[[[7-[2-(2-amino-4-thiazolyl) (methoxyimino)-acetamido]-2-carboxy-8-oxo-4-thia-1-azabicyclo[4,2,0]oct-2-en-3-yl]-methyl]-thio]-7-methyl-thieno[2,3-b]pyridinium U.V. Spectrum. (EtOH+0.1 N HCl)
Max. 228 nm $E^1_1$, $\epsilon=31,700$;
Inflexion 247 nm;
Max. 295 nm $E^1_1$, $\epsilon=19,500$;
Max. 330 nm $E^1_1$, $\epsilon=20,400$;
Inflexion 258, 288, 304 nm.

EXAMPLE 48

Internal salt of 2-[[[7-[2-(2-amino-4-thiazolyl)-2-(methoxyimino]-acetamido]-2-carboxy-8-oxo-4-thia-1-azabicyclo[4,2,0]oct-2-en-3-yl]-methyl]-thio]-1-bromo quinolizinium U.V. Spectrum. (EtOH)
Max. 224 nm $E^1_1=591$, $\epsilon=37,600$;
Max. 272 nm $E^1_1=354$, $\epsilon=22,500$;
Max. 294 nm $E^1_1=252$, $\epsilon=16,400$;
Inflexion 301 nm;
Inflexion 319 nm;
Max. 353 nm $E^1_1=304$, $\epsilon=19,300$;
Inflexion 360 nm $E^1_1=301$.
U.V. Spectrum. (EtOH+0.1 N HCl)
Max. 226 nm $E^1_1=529$, $\epsilon=33,600$;
Max. 270 nm $E^1_1=451$, $\epsilon=26,700$;
Max. 320 nm $E^1_1=293$, $\epsilon=18,600$;

Max. 353 nm $E^1_1=354$, $\epsilon=22,500$;
Inflexion 264, 292, 315, 358 nm.

EXAMPLE 49

Mixture of iodide and trifluoroacetate of 2-[[[7-[2-amino-4-thiazolyl)-(methoxyimino)-]acetamido]-2-carboxy-8-oxo-4-thia-1-azabicyclo[4,2,-0]oct-2-en-3-yl]-methyl]-thio]-pyridino[1,2-a]pyridinium (6S) (7S) (Z) (trifluoroacetate).

U.V. Spectrum. (EtOH)
Inflexion 220 nm;
Inflexion 260 nm;
Max. 310 nm $E^1_1=316$, $\epsilon=25,300$.
U.V. Spectrum. (EtOH+0.1 N HCl)
Inflexion 220 nm
Max. 262 nm $E^1_1=373$, $\epsilon=29,800$;
Max. 290 nm $E^1_1=317$, $\epsilon=25,400$;
Max. 316 nm $E^1_1=311$, $\epsilon=24,900$.

EXAMPLE 50

Injection preparations were made containing 500 mg of the product of Example 2 or Example 3 or Example 14 and sufficient excipient for a final volume of 5 ml.

PHARMACOLOGICAL STUDY OF THE INVENTION PRODUCTS

In Vitro Activity Method of Dilutions in Liquid Medium.

A series of tubes were prepared in each of which the same quantity of sterile nutritive medium was distributed and then in each tube, increasing quantities of the product under study were distributed after which each tube was inoculated with a bacterial strain. After incubation for 24 hours in an oven at 37° C., the inhibition of growth was determined by transillumination, which enabled the minimal inhibiting concentrations (M.I.C.) to be determined, expressed in μg/ml. The following results were obtained:

| STRAINS | Prod. Ex. 1 | Prod. Ex. 2 | Prod. Ex. 3 | Prod. Ex. 4 | Prod. Ex. 5 | Prod. Ex. 6 |
|---|---|---|---|---|---|---|
| STAPHYLOCOCCUS AUREUS SG511 | 10.000 | 0.300 | 1.200 | 1.200 | 0.600 | 10.000 |
| STAPHYLOCOCCUS AUREUS SG511 S | 5.000 | 0.300 | 0.600 | 2.500 | 1.200 | 20.000 |
| STAPHYLOCOCCUS AUREUS 285 | 10.000 | 0.150 | 0.300 | 0.600 | 0.600 | 10.000 |
| STAPHYLOCOCCUS AUREUS 54146 | 5.000 | 0.300 | 0.600 | 1.200 | 1.200 | 10.000 |
| STREPTOCOCCUS PYOGENES A 561 | ≦0.010 | ≦0.010 | 0.020 | ≦0.010 | 0.040 | 0.020 |
| STREPTOCOCCUS PYOGENES 77 A | 0.080 | 0.020 | ≦0.010 | ≦0.010 | ≦0.010 | 0.020 |
| STREPTOCOCCUS FAECIUM M 78 L | >20.000 | 2.500 | 5.000 | 2.500 | >20.000 | 20.000 |
| ESCHERICHIA COLI UC 1894 | 0.080 | ≦0.010 | ≦0.010 | ≦0.010 | ≦0.010 | 0.040 |
| ESCHERICHIA COLI O 78 | 0.300 | ≦0.010 | ≦0.010 | 0.040 | 0.020 | 0.300 |
| ESCHERICHIA COLI TEM | 0.600 | 0.040 | 0.020 | 0.080 | 0.040 | 0.600 |
| ESCHERICHIA COLI 1507 E | 0.150 | ≦0.010 | ≦0.010 | 0.020 | 0.020 | 0.080 |
| ESCHERICHIA COLI DC 0 | 1.200 | 0.040 | 0.040 | 0.080 | 0.150 | 1.200 |
| ESCHERICHIA COLI DC 2 | 0.300 | ≦0.010 | ≦0.010 | 0.020 | 0.020 | 0.080 |
| SALMONELLA TYPHIMURIUM MZ 11 | 0.300 | 0.020 | ≦0.010 | 0.040 | 0.040 | 0.600 |
| KLEBSIELLA PNEUMONIAE 52145 | 1.200 | 0.150 | 0.020 | 0.080 | 0.040 | 0.600 |
| KLEBSIELLA AEROGENES 1082 E | 20.000 | 0.300 | 0.300 | 1.200 | 1.200 | 20.000 |
| KLEBSIELLA AEROGENES 1522 E | 5.000 | 0.150 | 0.080 | 0.080 | 0.150 | 1.200 |
| ENTEROBACTER CLOACAE P 99 | >20.000 | 5.000 | 10.000 | >20.000 | 20.000 | >20.000 |
| ENTEROBACTER CLOACAE 1321 E | 0.600 | 0.020 | ≦0.010 | 0.020 | 0.040 | 0.600 |
| SERRATIA RG 2532 | 10.000 | 0.300 | 0.300 | 1.200 | 0.600 | 20.000 |
| PROTEUS MIRABILIS A 235 | 0.600 | 0.040 | 0.020 | 0.080 | 0.150 | 0.080 |
| PROTEUS VULGARIS A 232 | 0.600 | 0.040 | 0.020 | 0.080 | 0.300 | 0.300 |
| PROVIDENCIA DU 48 | 20.000 | 1.200 | 0.600 | 1.200 | 1.200 | 2.500 |

| STRAINS | Prod. Ex. 7 | Prod. Ex. 9 | Prod. Ex. 10 | Prod. Ex. 11 | Prod. Ex. 12 |
|---|---|---|---|---|---|
| STAPHYLOCOCCUS AUREUS SG511 | 10.000 | 0.600 | 1.200 | 0.300 | 0.600 |
| STAPHYLOCOCCUS AUREUS SG511 S | 20.000 | 0.600 | 2.500 | 0.300 | 1.200 |
| STAPHYLOCOCCUS AUREUS 285 | 10.000 | 0.600 | 0.600 | 0.150 | 0.600 |
| STAPHYLOCOCCUS AUREUS 54146 | 10.000 | 0.600 | 1.200 | 0.600 | 1.200 |
| STREPTOCOCCUS PYOGENES A 561 | 0.020 | 0.020 | ≦0.010 | 0.040 | ≦0.010 |
| STREPTOCOCCUS PYOGENES 77 A | 0.080 | ≦0.010 | ≦0.010 | 0.020 | 0.020 |
| STREPTOCOCCUS FAECIUM M 78 L | >20.000 | 1.200 | 10.000 | 1.200 | 10.000 |
| ESCHERICHIA COLI UC 1894 | 0.040 | 0.020 | 0.020 | ≦0.010 | ≦0.010 |
| ESCHERICHIA COLI O 78 | 0.150 | 0.600 | 0.040 | 0.020 | 0.020 |
| ESCHERICHIA COLI TEM | 0.300 | 0.600 | 0.150 | 0.040 | 0.150 |
| ESCHERICHIA COLI 1507 E | 0.080 | ≦0.010 | 0.020 | ≦0.010 | ≦0.010 |
| ESCHERICHIA COLI DC 0 | 0.600 | 0.300 | 0.080 | 0.080 | 0.150 |
| ESCHERICHIA COLI DC 2 | 0.080 | 0.600 | 0.020 | ≦3.010 | ≦0.010 |
| SALMONELLA TYPHIMURIUM MZ 11 | 0.150 | 0.600 | 0.080 | 0.020 | 0.040 |
| KLEBSIELLA PNEUMONIAE 52145 | 0.600 | 0.600 | 0.080 | 0.040 | 0.080 |
| KLEBSIELLA AEROGENES 1082 E | 10.000 | 0.600 | 0.600 | 0.600 | 0.300 |
| KLEBSIELLA AEROGENES 1522 E | 1.200 | 0.600 | 0.300 | 0.080 | 0.300 |
| ENTEROBACTER CLOACAE P 99 | >20.000 | 5.000 | 20.000 | 20.000 | 10.000 |
| ENTEROBACTER CLOACAE 1321 E | 0.300 | 0.150 | 0.150 | 0.040 | 0.040 |
| SERRATIA RG 2532 | 2.500 | 1.200 | 0.300 | 0.150 | 0.600 |
| PROTEUS MIRABILIS A 235 | 0.600 | 0.300 | 0.150 | 0.040 | 0.150 |
| PROTEUS VULGARIS A 232 | 0.600 | 0.300 | 0.150 | 0.080 | 0.080 |
| PROVIDENCIA DU 48 | 10.000 | 2.500 | 1.200 | 0.600 | 2.500 |

| STRAINS | Prod. Ex. 13 | Prod. Ex. 14 | Prod. Ex. 15 | Prod. Ex. 16 | Prod. Ex. 17 | Prod. Ex. 18 |
|---|---|---|---|---|---|---|
| STAPHYLOCOCCUS AUREUS SG511 | 0.600 | 0.600 | 10.000 | 20.000 | 1.200 | 2.500 |
| STAPHYLOCOCCUS AUREUS SG511 S | 0.600 | 2.500 | 10.000 | 20.000 | 1.200 | 2.500 |
| STAPHYLOCOCCUS AUREUS 285 | 0.150 | 0.300 | 10.000 | 20.000 | 1.200 | 0.600 |
| STAPHYLOCOCCUS AUREUS 54146 | 0.600 | 1.200 | 20.000 | >20.000 | 2.500 | 2.500 |

| -continued | | | | | | |
|---|---|---|---|---|---|---|
| STREPTOCOCCUS PYOGENES A 561 | 0.020 | 0.020 | 0.080 | 0.020 | ≦0.010 | 0.020 |
| STREPTOCOCCUS PYOGENES 77 A | 0.040 | ≦0.010 | 0.040 | 0.080 | ≦0.010 | 0.020 |
| STREPTOCOCCUS FAECIUM M 78 L | 20.000 | 2.500 | >20.000 | >20.000 | 5.000 | 10.000 |
| ESCHERICHIA COLI UC 1894 | ≦0.010 | ≦0.010 | 0.300 | 0.020 | ≦0.010 | ≦0.010 |
| ESCHERICHIA COLI O 78 | 0.800 | ≦0.010 | 0.600 | 0.150 | 0.020 | 0.080 |
| ESCHERICHIA COLI TEM | 0.300 | 0.020 | 1.200 | 0.080 | 0.300 | 0.150 |
| ESCHERICHIA COLI 1507 E | ≦0.010 | ≦0.010 | 0.150 | 0.020 | 0.020 | 0.040 |
| ESCHERICHIA COLI DC 0 | 0.300 | 0.040 | 1.200 | 0.080 | 0.300 | 0.150 |
| ESCHERICHIA COLI DC 2 | ≦0.010 | ≦0.010 | 0.300 | 0.080 | 0.010 | 0.020 |
| SALMONELLA TYPHIMURIUM MZ 11 | 0.150 | 0.040 | 0.600 | 0.040 | 0.040 | 0.080 |
| KLEBSIELLA PNEUMONIAE 52145 | 0.300 | 0.020 | 1.200 | 0.150 | 0.600 | 0.150 |
| KLEBSIELLA AEROGENES 1082 E | 1.200 | 1.200 | 5.000 | 10.000 | 0.600 | 2.500 |
| KLEBSIELLA AEROGENES 1522 E | 0.600 | 0.150 | 1.200 | 0.600 | 0.600 | 0.600 |
| ENTEROBACTER CLOACAE P 99 | 20.000 | 2.500 | >20.000 | >20.000 | 20.000 | 20.000 |
| ENTEROBACTER CLOACAE 1321 E | 0.300 | 0.020 | 0.600 | 0.040 | 0.040 | 0.150 |
| SERRATIA RG 2532 | 2.500 | 0.080 | 10.000 | 0.300 | 0.300 | 0.300 |
| PROTEUS MIRABILIS A 235 | 0.300 | 0.040 | 0.600 | 0.040 | 0.150 | 0.150 |
| PROTEUS VULGARIS A 232 | 0.150 | 0.040 | 1.200 | 0.150 | 0.150 | 0.300 |
| PROVIDENCIA DU 48 | 5.000 | 0.600 | 20.000 | 1.200 | 2.500 | 2.500 |

| STRAINS | Prod. Ex. 19 | Prod. Ex. 20 | Prod. Ex. 21 | Prod. Ex. 22 | Prod. Ex. 23 | Prod. Ex. 24 |
|---|---|---|---|---|---|---|
| STAPHYLOCOCCUS AUREUS SG511 | 1.200 | 0.600 | 2.500 | 0.600 | 0.300 | 20.000 |
| STAPHYLOCOCCUS AUREUS SG511 S | 1.200 | 0.600 | 2.500 | 0.600 | 0.300 | 20.000 |
| STAPHYLOCOCCUS AUREUS 285 | 0.600 | 0.300 | 1.200 | 0.600 | 0.300 | 20.000 |
| STAPHYLOCOCCUS AUREUS 54146 | 1.200 | 0.600 | 2.500 | 1.200 | 0.600 | >20.000 |
| STREPTOCOCCUS PYOGENES A 561 | 0.020 | 0.020 | ≦0.010 | ≦0.010 | ≦0.010 | 0.080 |
| STREPTOCOCCUS PYOGENES 77 A | 0.020 | 0.020 | ≦0.010 | ≦0.010 | ≦0.010 | 0.040 |
| STREPTOCOCCUS FAECIUM M 78 L | 2.500 | 2.500 | 20.000 | 5.000 | 2.500 | >20.000 |
| ESCHERICHIA COLI UC 1894 | ≦0.010 | ≦0.010 | ≦0.010 | ≦0.010 | ≦0.010 | 0.040 |
| ESCHERICHIA COLI O 78 | 0.020 | 0.020 | 0.040 | 0.020 | 0.040 | 0.150 |
| ESCHERICHIA COLI TEM | 0.150 | 0.080 | 0.150 | 0.040 | 0.150 | 0.300 |
| ESCHERICHIA COLI 1507 E | ≦0.010 | ≦0.010 | ≦0.010 | ≦0.010 | ≦0.010 | 0.080 |
| ESCHERICHIA COLI DC 0 | 0.080 | 0.080 | 0.150 | 0.040 | 0.150 | 0.300 |
| ESCHERICHIA COLI DC 2 | 0.020 | ≦0.010 | 0.020 | ≦0.010 | ≦0.010 | 0.080 |
| SALMONELLA TYPHIMURIUM MZ 11 | 0.150 | 0.080 | 0.040 | 0.020 | 0.040 | 0.300 |
| KLEBSIELLA PNEUMONIAE 52145 | 0.080 | 0.080 | 0.150 | 0.040 | 0.300 | 0.150 |
| KLEBSIELLA AEROGENES 1082 E | 2.500 | 0.600 | 1.200 | 0.300 | 1.200 | >20.000 |
| KLEBSIELLA AEROGENES 1522 E | 0.150 | 0.300 | 0.300 | 0.150 | 0.300 | 0.300 |
| ENTEROBACTER CLOACAE P 99 | 10.000 | 10.000 | 20.000 | 20.000 | 10.000 | >20.000 |
| ENTEROBACTER CLOACAE 1321 E | 0.080 | 0.080 | 0.080 | 0.020 | 0.080 | 0.600 |
| SERRATIA RG 2532 | 1.250 | 0.600 | 0.300 | 0.600 | 1.200 | 1.200 |
| PROTEUS MIRABILIS A 235 | 0.300 | 0.150 | 0.150 | 0.080 | 0.300 | 0.600 |
| PROTEUS VULGARIS A 232 | 0.300 | 0.300 | 0.150 | 0.080 | 0.150 | 0.300 |
| PROVIDENCIA DU 48 | 2.500 | 1.200 | 5.000 | 1.200 | 2.500 | 2.500 |

| STRAINS | Prod. Ex. 25 | Prod. Ex. 26 | Prod. Ex. 27 | Prod. Ex. 28 | Prod. Ex. 29 | Prod. Ex. 30 |
|---|---|---|---|---|---|---|
| STAPHYLOCOCCUS AUREUS SG511 | 0.600 | 2.500 | 0.300 | 5.000 | 2.500 | 0.300 |
| STAPHYLOCOCCUS AUREUS SG511 S | 1.200 | 5.000 | 0.300 | 5.000 | 5.000 | 0.300 |
| STAPHYLOCOCCUS AUREUS 285 | 0.600 | 2.500 | 0.150 | 5.000 | 2.500 | 0.300 |
| STAPHYLOCOCCUS AUREUS 54146 | 1.200 | 5.000 | 0.300 | 5.000 | 5.000 | 0.600 |
| STREPTOCOCCUS PYOGENES A 561 | 0.020 | 0.080 | ≦0.010 | 0.300 | 0.300 | ≦0.010 |
| STREPTOCOCCUS PYOGENES 77 A | ≦0.010 | 0.040 | ≦0.010 | 0.300 | 0.300 | ≦0.010 |
| STREPTOCOCCUS FAECIUM M 78 L | 2.500 | 20.000 | 1.250 | >20.000 | >20.000 | 2.500 |
| ESCHERICHIA COLI UC 1894 | ≦0.010 | ≦0.010 | ≦0.010 | 0.040 | 0.080 | ≦0.010 |
| ESCHERICHIA COLI O 78 | 0.020 | 0.080 | 0.020 | 0.600 | 0.150 | 0.040 |
| ESCHERICHIA COLI TEM | 0.080 | 0.040 | 0.080 | 0.300 | 0.300 | 0.150 |
| ESCHERICHIA COLI 1507 E | ≦0.010 | 0.020 | ≦0.010 | 0.080 | 0.080 | ≦0.010 |
| ESCHERICHIA COLI DC 0 | 0.150 | 0.040 | 0.040 | 0.150 | 0.150 | 0.300 |
| ESCHERICHIA COLI DC 2 | ≦0.010 | 0.080 | ≦0.010 | 0.150 | 0.040 | ≦0.010 |
| SALMONELLA TYPHIMURIUM MZ 11 | 0.040 | 0.150 | 0.020 | 0.150 | 0.150 | 0.080 |
| KLEBSIELLA PNEUMONIAE 52145 | 0.080 | 0.020 | 0.040 | 0.300 | 0.150 | 0.150 |
| KLEBSIELLA AEROGENES 1082 E | 5.000 | >20.000 | 5.000 | 1.200 | 0.600 | 2.500 |
| KLEBSIELLA AEROGENES 1522 E | 0.150 | 0.150 | 0.300 | 0.300 | 0.300 | 0.150 |
| ENTEROBACTER CLOACAE P 99 | >20.000 | >20.000 | 10.000 | >20.000 | >20.000 | 20.0000 |
| ENTEROBACTER CLOACAE 1321 E | 0.150 | 0.080 | 0.020 | 0.150 | 0.150 | 0.080 |
| SERRATIA RG 2532 | 1.200 | 1.200 | 1.200 | 0.600 | 0.600 | 1.200 |
| PROTEUS MIRABILIS A 235 | 0.150 | 0.040 | 0.080 | 0.080 | 0.080 | 0.300 |
| PROTEUS VULGARIS A 232 | 0.300 | 0.600 | 0.600 | 0.020 | 0.040 | 0.300 |
| PROVIDENCIA DU 48 | 1.200 | 1.200 | 1.200 | 2.500 | 2.500 | 1.200 |

| STRAINS | Prod. Ex. 31 | Prod. Ex. 32 | Prod. Ex. 33 | Prod. Ex. 34 | Prod. Ex. 35 | Prod. Ex. 36 |
|---|---|---|---|---|---|---|
| STAPHYLOCOCCUS AUREUS SG511 | 0.150 | 0.150 | 1.200 | 0.600 | 1.200 | 0.150 |
| STAPHYLOCOCCUS AUREUS SG511 S | 0.300 | 0.300 | 1.200 | 0.600 | 0.600 | 0.300 |
| STAPHYLOCOCCUS AUREUS 285 | 0.150 | 0.150 | 0.600 | 0.600 | 1.200 | 0.150 |
| STAPHYLOCOCCUS AUREUS 54146 | 0.300 | 0.300 | 1.200 | 1.200 | 1.200 | 0.300 |
| STREPTOCOCCUS PYOGENES A 561 | ≦0.010 | 0.020 | 0.040 | 0.020 | 0.020 | ≦0.010 |
| STREPTOCOCCUS PYOGENES 77 A | ≦0.010 | ≦0.010 | 0.040 | ≦0.010 | 0.020 | ≦0.010 |
| STREPTOCOCCUS FAECIUM M 78 L | 20.000 | 5.000 | 20.000 | 5.000 | >20.000 | 1.200 |
| ESCHERICHIA COLI UC 1894 | 0.020 | 0.040 | ≦0.010 | 0.080 | 0.020 | ≦0.010 |

-continued

| STRAINS | | | | | | |
|---|---|---|---|---|---|---|
| ESCHERICHIA COLI O 78 | 0.300 | 0.300 | 0.040 | 0.150 | 0.080 | 0.020 |
| ESCHERICHIA COLI TEM | 0.600 | 1.200 | 0.080 | 0.300 | 0.150 | 0.040 |
| ESCHERICHIA COLI 1507 E | ≦0.010 | ≦0.010 | 0.020 | 0.150 | 0.040 | ≦0.010 |
| ESCHERICHIA COLI DC 0 | 1.200 | 1.200 | 0.080 | 0.300 | 0.150 | 0.080 |
| ESCHERICHIA COLI DC 2 | ≦0.010 | ≦0.010 | 0.020 | 0.300 | 0.080 | ≦0.010 |
| SALMONELLA TYPHIMURIUM MZ 11 | 0.600 | 0.600 | 0.080 | 0.150 | 0.040 | ≦0.010 |
| KLEBSIELLA PNEUMONIAE 52145 | 1.200 | 2.500 | 0.080 | 0.300 | 0.150 | 0.150 |
| KLEBSIELLA AEROGENES 1082 E | 2.500 | 20.000 | 0.600 | >20.000 | 10.000 | 1.200 |
| KLEBSIELLA AEROGENES 1522 E | 2.500 | 2.500 | 0.300 | 0.300 | 0.600 | 0.150 |
| ENTEROBACTER CLOACAE P 99 | 20.000 | 20.000 | 10.000 | >20.000 | >20.000 | 10.000 |
| ENTEROBACTER CLOACAE 1321 E | 0.300 | 0.300 | 0.080 | 0.600 | 0.300 | 0.040 |
| SERRATIA RG 2532 | 2.500 | 5.000 | 0.600 | 1.200 | 1.200 | 0.300 |
| PROTEUS MIRABILIS A 235 | 0.600 | 0.600 | 0.150 | 1.200 | 0.600 | 0.080 |
| PROTEUS VULGARIS A 232 | 0.600 | 1.200 | 0.150 | 10.000 | 1.200 | 0.150 |
| PROVIDENCIA DU 48 | 5.000 | 5.000 | 2.500 | 2.500 | 2.500 | 1.200 |

| STRAINS | Prod. Ex. 38 |
|---|---|
| STAPHYLOCOCCUS AUREUS SG511 | 0.300 |
| STAPHYLOCOCCUS AUREUS SG511 S | 0.300 |
| STAPHYLOCOCCUS AUREUS 285 | 0.300 |
| STAPHYLOCOCCUS AUREUS 54146 | 0.300 |
| STREPTOCOCCUS PYOGENES A 561 | ≦0.010 |
| STREPTOCOCCUS PYOGENES 77 A | ≦0.010 |
| STREPTOCOCCUS FAECIUM M 78 L | 1.200 |
| ESCHERICHIA COLI UC 1894 | ≦0.010 |
| ESCHERICHIA COLI O 78 | 0.020 |
| ESCHERICHIA COLI TEM | 0.080 |
| ESCHERICHIA COLI 1507 E | ≦0.010 |
| ESCHERICHIA COLI DC 0 | 0.150 |
| ESCHERICHIA COLI DC 2 | ≦0.010 |
| SALMONELLA TYPHIMURIUM MZ 11 | 0.080 |
| KLEBSIELLA PNEUMONIAE 52145 | 0.150 |
| KLEBSIELLA AEROGENES 1082 E | 5.000 |
| KLEBSIELLA AEROGENES 1522 E | 0.300 |
| ENTEROBACTER CLOACAE P 99 | 20.000 |
| ENTEROBACTER CLOACAE 1321 E | 0.040 |
| SERRATIA RG 2532 | 0.600 |
| PROTEUS MIRABILIS A 235 | 0.080 |
| PROTEUS VULGARIS A 232 | 0.300 |
| PROVIDENCIA DU 48 | 1.200 |

Various modifications of the products and method of the invention may be made without departing from the spirit or scope thereof and it is to be understood that the invention is to be limited only as defined in the appended claims.

What is claim is:

1. A compound selected from the group consisting of 1-dethia-2-thia-cephalosporanic acids of the formula

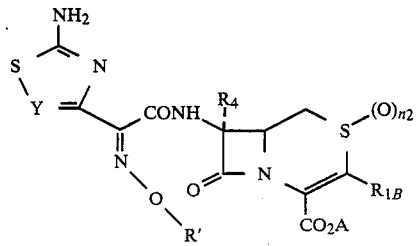

wherein $R'$ is selected from the group consisting of hydrogen, alkyl of 1 to 6 carbon atoms, alkenyl and alkynyl of 2 to 6 carbon atoms, and cycloalkyl of 3 to 6 carbon atoms substituted or unsubstituted with at least one member of the group consisting of halogen, carboxy, salified carboxy, esterified carboxy, alkoxy, oxo, alkylthio, mercapto, hydroxy, amino, nitro, carbamoyl and cyano, $n_2$ is 0, 1 or 2, $R_4$ is hydrogen or methoxy, $R_{1B}$ is —$(CH=CH)_{n1}$—$CH_2$—S—$R_m$, $n_1$ is 0, 1 or 2, $R_m$ is an unsaturated group including a positively charged and double bonded nitrogen atom, the said group being bonded to the sulfur atom through a carbon atom and selected from the group consisting of pyridyl, pyrrolyl, oxazolyl, thiazolyl, imidazolyl, pyrazolyl, triazolyl, tetrazolyl, pyridazinyl, pyrimidinyl, pyrazinyl, quinoleinyl, isoquinoleinyl, cinnolinyl, quanazolinyl, pyridino pyrimidinyl, dihydro- or tetrahydro-pyridyl, unsubstituted or substituted by at least one member selected from the group of alkyl of 1 to 4 carbon atoms, methoxy, ethoxy, halogen, carboxyalkyl, esterified carboxyalkyl, carbamoyl, thioacetylalkyl, thiocarbamoylalkyl, haloalkyl, cyanoalkyl and alkenyl of 2 to 4 carbon atoms Y is methine or nitrogen and A is selected from the group consisting of hydrogen, alkali metal ion, or alkaline earth metal ion, magnesium ion, ammonium ion, an organic amine base and an ester group or —COOA is —COO⁻ and their non-toxic, pharmaceutically acceptable acid addition salts.

2. A compound of claim 1 selected from the group consisting of compounds of the formula

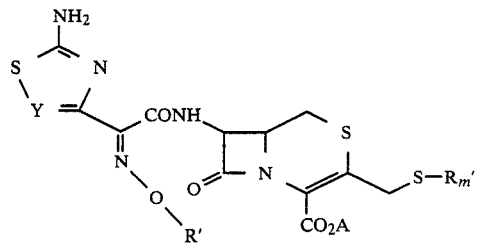

syn isomer, wherein $R'$ is hydrogen or alkyl, alkenyl, alkynyl or cycloalkyl of up to 6 carbon atoms or aryl, $R_m$ is pyridinium unsubstituted or substituted as in claim 1 or, partially hydrogenated and bonded to the sulfur atom through a carbon atom, Y is methine or nitrogen and A has the definition of claim 1 and its non-toxic, pharmaceutically acceptable acid addition salts.

3. A compound of claim 1 selected from the group consisting of compound of the formula

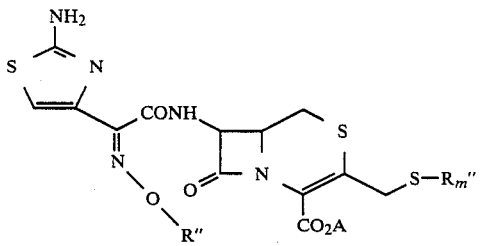

in which R'' is methyl, fluoromethyl or difluoromethyl, $R_m''$ is

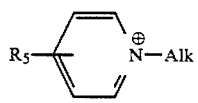

in which Alk is alkyl of 1 to 4 carbon atoms, $R_5$ is hydrogen, alkyl or alkythio of 1 to 4 carbon atoms, $R_m''$ is bonded to the sulfur atom by the positions 2 or 4 and A has the definition of claim 1 and its non-toxic, pharmaceutically acceptable acid addition salts.

4. A compound of claim 1 selected from the group consisting of (6S) (7S) (Z) 4-[[[7-[(2-amino-4-thiazolyl)[-(difluoromethoxy)-imino]-acetamido]-2-carboxy-8-oxo-4-thia-1-azabicyclo[4,2,0]oct-2-en-3-yl]-methyl]-thio]-1-methyl pyridinium, (6S) (7S) (Z) 4-[[[7-[(2-amino-4-thiazolyl)-[(fluoromethoxy)imino]-acetamido]-2-carboxy-8-oxo-4-thia-1-azabicyclo[4,2,0]oct-2-en-3-yl]-methyl]-1-methyl pyridinium, (6S) (7S) (Z) 2-[[[7-[2-amino-4-thiazolyl)-(fluoromethoxy)imino]-acetamido]-2-carboxy-8-oxo-4-thia-1-azabicyclo[4,2,-0]oct-2-en-3-yl]-methyl]-thio]-1-methyl pyridinium, 4 -[[[7-[[2-(2-amino-4-thiazolyl)-2-(methoxy)imino]-acetamido]-2-carboxy-8-oxo-4-thia-1-azabicyclo[4,2,-0]oct-2-en-3-yl]-methyl]thio]-1-ethyl-3-methyl pyridinium, (6S) (7S) (Z), 4-[[[7-[[2-(2-amino-4-thiazolyl)-2-(methoxy)imino]-acetamido]-2-carboxy-8-oxo-4-thia-1-azabicyclo[4,2,0]oct-2-en-3-yl]methyl]-thio]-1,3-dimethyl pyridinium, (6S) (7S) (Z), 4-[[[7-[[2-(2-amino-4-thiazolyl)(methoxy)-imino]-acetamido]-2-carboxy-8-oxo-4-thia-1-azabicyclo[4,2,0]oct-2-en-3-yl]-methyl]-thio]-1-methyl pyridinium, (6S) (7S) (Z), 4-[[[7-[[2-(2-amino-4-thiazolyl) (methoxy)imino]-acetamido]-2-carboxy-8-oxo-4-thia-1-azabicyclo[4,2,0]oct-2-en-3-yl]-methyl]thio]-1-methyl-5,6-dihydro pyridinium, (6S) (7S) (Z), in the form of an internal salt and their non-toxic, pharmaceutically acceptable acid addition salts.

5. A compound of claim 1 selected from the group consisting of (6S) (7S) (Z) 4-[[[7-[(2-amino-4-thiazolyl)[-(difluoromethoxy)imino]-acetamido]-2-carboxy-8-oxo-4-thia-1-azabicyclo[4,2,0]oct-2-en-3-yl]-methyl]-thio]-1-methyl pyridinium in the form of an internal salt and its non-toxic, pharmaceutically acceptable acid addition salts.

6. An antibacterial composition comprising an bactericidally effective amount of at least one compound of claim 1 and an inert pharmaceutical carrier.

7. A composition of claim 6 wherein the active compound is selected from the group consisting of compounds of the formula

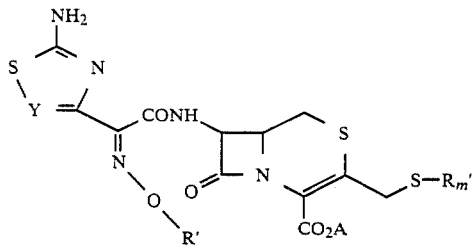

syn isomer wherein R' is hydrogen or alkyl, alkenyl, alkynyl or cycloalkyl of up to 6 carbon atoms or aryl, $R_m'$ is pyridinium unsubstituted or substituted as in claim 1 or partially hydrogenated and bonded to the sulfur atom through a carbon atom, Y is methine or nitrogen and A has the definition of claim 1 and its non-toxic, pharmaceutically acceptable acid addition salts.

8. A composition of claim 6 wherein the active compound is selected from the group consisting of compounds of the formula

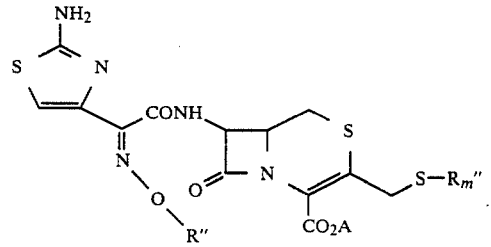

in which R'' is methyl, fluoromethyl or difluoromethyl, $R_m''$ is

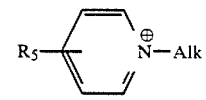

in which Alk is alkyl of 1 to 4 carbon atoms, $R_5$ is hydrogen, alkyl or alkylthio of 1 to 4 carbon atoms, $R_m''$ is bonded to the sulfur atom by the positions 2 or 4 and A has the definition of claim 1 and its non-toxic, pharmaceutically acceptable acid addition salts.

9. A composition of claim 6 wherein the active compound is selected from the group consisting of (6S) (7S) (Z) 4-[[[7-[(2-amino-4-thiazolyl)-[(difluoromethoxy)imino]-acetamido]-2-carboxy-8-oxo-4-thia-1-azabicyclo[4,2,0]oct-2-en-3-yl]-methyl]-thio]-1-methyl pyridinium, (6S) (7S) (Z) 4-[[[7-[(2-amino-4-thiazolyl)-[(fluoromethoxy)imino]-acetamido]-2-carboxy-8-oxo-4-thia-1-azabicyclo[4,2,0]oct-2-en-3-yl]-methyl]-thio]-1-methyl pyridinium, (6S) (7S) (Z) 2-[[[7-[[(2-amino-4-thiazolyl)-(fluoromethoxy)imino]acetamido]-2-carboxy-8-oxo-4-thia-1-azabicyclo[4,2,0]oct-2-en-3-yl]-methyl]-thio]-1-methyl pyridinium, 4-[[[7-[[2-(2-amino-4-thiazolyl)-2-(methoxy)imino]-acetamido]-2-carboxy-8-oxo-4-thia-1-azabicylco[4,2,0]oct-2-en-3-yl]-methyl]-thio]-1-ethyl-3-methyl pyridinium, (6S) (7S) (Z), 4-[[[7-[[2-(2-amino-4-thiazolyl)-2-(methoxy)imino]-acetamido]-2-carboxy-8-oxo-4-thia-1-azabicyclo[4,2,-0]oct-2-en-3-yl]-methyl]thio]-1,3-dimethyl pyridinium, (6S) (7S) (Z) 4-[[[7-[[2-(2-amino-4-thiazolyl) (methoxy)imino]-acetamido]-2-carboxy-8-oxo-4-thia-1-azabicyclo[4,2,0]oct-2-en-3-yl]-methyl]thio]-1-methyl pyridinium, (6S) (7S) (Z), 4-[[[7-[[2-(2-amino-4-thiazolyl) (methoxy)imino]acetamido]-2-carboxy-8-oxo-4-thia-1-azabicyclo[4,2,0]oct-2-en-3-yl]-methyl]thio]-1-methyl-5,6-dihydro pyridinium, (6S) (7S) (Z), in the form of an internal salt and their non-toxic, pharmaceutically acceptable acid addition salts.

10. A composition of 6 claim wherein the active compound is selected from group consisting of (6S) (7S) (Z) 4-[[[7-[(2-amino-4-thiazolyl)-[(difluoromethoxy)imino]-acetamido]-2-carboxy-8-oxo-4-thia-1-azabicyclo[4,2,-0]oct-2-en-3-yl]-methyl]-thio]-1-methyl pyridinium in the form of an internal salt and its non-toxic, pharmaceutically acceptable acid addition salts.

11. A method of combatting bacterial infections in warm-blooded animals comprising administering to warm-blooded animals a bactericidally effective amount of at least one compound of claim 1.

12. A method of claim 11 wherein the active compound is selected from the group consisting of compounds of the formula

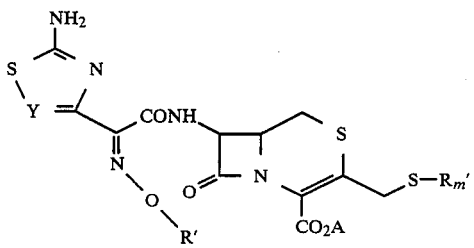

syn isomer wherein R' is hydrogen or alkyl, alkenyl, alkynyl or cycloalkyl of up to 6 carbon atoms or aryl, $R_m$ is pyridinium unsubstituted or substituted as in claim 1 or partially hydrogenated and bonded to the sulfur atom through a carbon atom, Y is methine or nitrogen and A has the definition of claim 1 and its non-toxic, pharmaceutically acceptable acid addition salts.

13. A method of claim 11 wherein the active compound is selected from the group consisting of compounds of the formula

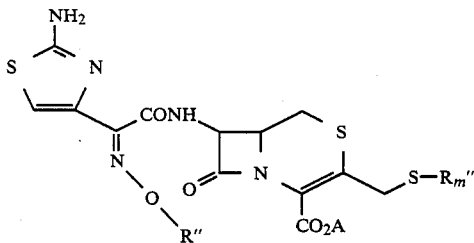

in which R" is methyl, fluoromethyl or difluoromethyl $R_m''$ is

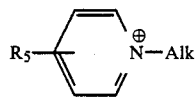

in which Alk is alkyl of 1 to 4 carbon atoms, $R_5$ is hydrogen, alkyl or alkylthio of 1 to 4 carbon atoms, $R_m''$ is bonded to the sulfur atom by the positions 2 or 4 and A has the defintion of claim 1 and its non-toxic, pharmaceutically acceptable acid addition salts.

14. A method of claim 11 selected from the group consisting of (6S) (7S) (Z) 4-[[[7-[(2-amino-4-thiazolyl)-[(difluoromethoxy)imino]-acetamido]-2-carboxy-8-oxo-4-thia-1-azabicyclo[4,2,0]oct-2-en-3-yl]-methyl]-thio]-1-methyl pyridinium, (6S) (7S) (Z) 4-[[[7-[(2-amino-4-thiazolyl)-[(fluoromethoxy)imino]-acetamido]-2-carboxy-8-oxo-4-thia-1-azabicyclo[4,2,0]oct-2-en-3-yl]-methyl]-thio]-1-methyl pyridinium (6S) (7S) (Z) 2-[[[7-[(2-amino-4-thiazolyl)-(fluoromethoxy) imino]-acetamido]-2-carboxy-8-ox-4-thia-1-azabicyclo[4,2,0]oct-2-en-3-yl]-methyl]-thio]-1-methyl pyridinium, 4-[[[7-[2-(2-amino-4-thiazolyl)-2-(methoxy)imino]-acetamido]-2-carboxy-8-oxo-4-thia-1-azabicyclo[4,2,0]oct-2-en-3-yl]methyl]-thio]-1-ethyl-3-methyl pyridinium, (6S) (7S) (Z) 4-[[[7-[2-(2-amino-4-thiazolyl)-2-(methoxy)imino]-acetamido]2-carboxy-8-oxo-4-thia-1-azabicyclo[4,2,0]oct-2-en-3-yl]methyl]-thio]-1,3-dimethyl pyridinium, (6S) (7S) (Z) 4-[[[7-[2-amino-4-thiazolyl)(methoxy)imino]-acetamido]-2-carboxy-8-oxo-4-thia-1-azabicyclo[4,2,0]oct-2-en-3-yl]methyl]-thio]-1-methyl pyridinium (6S) (7S) (Z) 4-[[[7-[2-(2-amino-4-thiazolyl) (methoxy)imino]-acetamido]-2-carboxy-8-oxo-4-thia-1-azabicyclo[4,2,0]oct-2-en-3-yl]methyl]-thio]-1-methyl-5,6-dihydro pyridinium (6S) (7S) (Z), in the form of an internal salt and their non-toxic, pharmaceutically acceptable acid addition salts.

15. A method of claim 11 wherein the active compound is selected from the group consisting of (6S) (7S) (Z) 4-[[[7-[(2-amino-4-thiazolyl)[(difluoromethoxy)imino]-acetamido]-2-carboxy-8-oxo-4-thia-1-azabicyclo[4,2,0]oct-2-en-3-yl]-methyl]-thio]-1-methyl pyridinium in the form of an internal salt and its non-toxic, pharmaceutically acceptable acid addition salts.

* * * * *